(12) United States Patent
Moore

(10) Patent No.: US 10,487,297 B2
(45) Date of Patent: *Nov. 26, 2019

(54) ENVIRONMENTALLY PREFERRED ANTIMICROBIAL COMPOSITIONS

(71) Applicant: CHEMLINK LABORATORIES, LLC, Kennesaw, GA (US)

(72) Inventor: Ryan Giffin Moore, Lilburn, GA (US)

(73) Assignee: CHEMLINK LABORATORIES, LLC, Kennesaw, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,555

(22) Filed: Jun. 1, 2017

(65) Prior Publication Data

US 2017/0267952 A1 Sep. 21, 2017

Related U.S. Application Data

(63) Continuation of application No. 14/500,473, filed on Sep. 29, 2014, now Pat. No. 9,701,931.

(60) Provisional application No. 61/885,211, filed on Oct. 1, 2013, provisional application No. 61/884,226, filed on Sep. 30, 2013.

(51) Int. Cl.

| | |
|---|---|
| C11D 3/48 | (2006.01) |
| C11D 3/39 | (2006.01) |
| A01N 37/16 | (2006.01) |
| C11D 11/00 | (2006.01) |
| A01N 59/00 | (2006.01) |
| A01N 25/22 | (2006.01) |
| C11D 3/20 | (2006.01) |
| A01N 25/26 | (2006.01) |
| A01N 25/34 | (2006.01) |
| A01N 37/36 | (2006.01) |
| A01N 37/46 | (2006.01) |
| C11D 7/26 | (2006.01) |

(52) U.S. Cl.
CPC .............. C11D 3/48 (2013.01); A01N 37/16 (2013.01); A01N 59/00 (2013.01); C11D 3/2075 (2013.01); C11D 3/391 (2013.01); C11D 3/3917 (2013.01); C11D 7/265 (2013.01); C11D 11/0017 (2013.01); C11D 11/0023 (2013.01); C11D 11/0041 (2013.01)

(58) Field of Classification Search
CPC ......... C11D 3/48; C11D 3/2075; C11D 3/391; C11D 11/0023; C11D 11/0017; C11D 11/0041; C11D 7/265; C11D 3/3917; A01N 37/16; A01N 59/00; A01N 25/26; A01N 25/34; A01N 37/36; A01N 37/46; A01N 25/22

See application file for complete search history.

(56) References Cited

U.S. PATENT DOCUMENTS

| | | | |
|---|---|---|---|
| 2,760,942 A | 8/1956 | Oakley et al. | |
| 3,086,007 A | 4/1963 | Touey et al. | |
| 3,198,740 A | 8/1965 | Dunlop et al. | |
| 3,374,195 A | 3/1968 | Bianco et al. | |
| 3,413,229 A | 11/1968 | Bianco et al. | |
| 3,892,905 A | 7/1975 | Albert | |
| 3,926,830 A * | 12/1975 | Horiguchi ............. | C09B 69/103 436/163 |
| 4,155,971 A | 5/1979 | Wysong | |
| 4,340,491 A | 7/1982 | Lee | |
| 4,412,934 A | 11/1983 | Chung et al. | |
| 4,416,791 A | 11/1983 | Haq | |
| 4,473,507 A | 9/1984 | Bossu | |
| 4,608,187 A | 8/1986 | Chang | |
| 4,626,372 A | 12/1986 | Kaufmann et al. | |
| 4,634,551 A | 1/1987 | Burns et al. | |
| 4,915,854 A | 4/1990 | Mao et al. | |
| 4,966,723 A | 10/1990 | Hodge | |
| 5,224,601 A | 7/1993 | Gouge et al. | |
| 5,505,740 A | 4/1996 | Kong et al. | |
| 5,688,516 A | 11/1997 | Raad et al. | |
| 5,716,007 A | 2/1998 | Nottingham et al. | |

(Continued)

FOREIGN PATENT DOCUMENTS

| | | | | |
|---|---|---|---|---|
| EP | 0427314 B1 * | 12/1995 | ............... | C11D 3/10 |
| EP | 0427314 B1 | 12/1995 | | |

(Continued)

OTHER PUBLICATIONS

Office Action of the U.S. Patent Office in U.S. Appl. No. 14/500,473, dated Sep. 8, 2015.

(Continued)

Primary Examiner — Doan T Phan
(74) Attorney, Agent, or Firm — Dentons US LLP; Frank J. Miskiel

(57) ABSTRACT

Provided are antimicrobial compositions that include a hydrogen peroxide generator, a peracid catalyst, a sugar acid lactone selected from among a gluconolactone, a galactonolactone, a mannonolactone, a gulonolactone and a combination thereof in an amount from about 10 wt % to about 60 wt %, an acetate, and a carboxylic acid, where the ratio between the hydrogen peroxide generator and the peracetic acid catalyst is from about 1.5:1 to about 3:1 respectively. The compositions have increased shelf life and storage stability. The antimicrobial compositions can be formulated into a disinfection solution. Also provided are methods of disinfecting a surface that include applying the disinfecting solution to a surface, resulting in the destruction of a microbe on the surface.

19 Claims, No Drawings

(56) References Cited

U.S. PATENT DOCUMENTS

| | | | |
|---|---|---|---|
| 5,716,008 A | 2/1998 | Nottingham et al. | |
| 5,975,095 A | 11/1999 | Ahmed et al. | |
| 6,080,710 A | 6/2000 | Withenshaw et al. | |
| 6,225,276 B1* | 5/2001 | Gassenmeier | C11D 3/0047 510/376 |
| 6,407,052 B2 | 6/2002 | Gassenmeier et al. | |
| 6,655,837 B2 | 12/2003 | Matsuda et al. | |
| 6,995,126 B2 | 2/2006 | Perkis et al. | |
| 7,013,623 B2 | 3/2006 | Fisher et al. | |
| 7,036,986 B2 | 5/2006 | Matsuda et al. | |
| 7,235,252 B2 | 6/2007 | Preto et al. | |
| 7,569,530 B1 | 8/2009 | Pan et al. | |
| 8,568,613 B2 | 10/2013 | Man et al. | |
| 9,701,931 B2 | 7/2017 | Moore | |
| 2004/0072716 A1* | 4/2004 | Kistenmacher | C11D 3/3757 510/475 |
| 2005/0113279 A1 | 5/2005 | Desmarescaux et al. | |
| 2008/0293607 A1 | 11/2008 | Jones et al. | |
| 2009/0074881 A1 | 3/2009 | Kielbania, Jr. | |
| 2012/0219513 A1* | 8/2012 | Moore | C01B 15/103 424/53 |
| 2013/0061883 A1* | 3/2013 | Miravet Celades | A61K 8/38 134/26 |
| 2015/0093425 A1 | 4/2015 | Moore | |

FOREIGN PATENT DOCUMENTS

| | | |
|---|---|---|
| WO | 2002042400 A2 | 5/2002 |
| WO | 2008087424 A1 | 7/2008 |

OTHER PUBLICATIONS

Response in U.S. Appl. No. 14/500,473, filed Sep. 29, 2015.
Office Action of the U.S. Patent Office in U.S. Appl. No. 14/500,473, dated Dec. 16, 2015.
Request for Continued Examination in U.S. Appl. No. 14/500,473, filed Mar. 14, 2016.
Office Action of the U.S. Patent Office in U.S. Appl. No. 14/500,473, dated Jul. 19, 2016.
Response and Second Declaration of Mr. Moore in U.S. Appl. No. 14/500,473, filed Nov. 16, 2016.
Notice of Allowance of the U.S. Patent Office in U.S. Appl. No. 14/500,473, dated Mar. 8, 2017.
Notice of Allowance of the Mexican Patent Office in Appl'n No. MX/a/2014/011710, dated Jul. 14, 2017.

* cited by examiner

ENVIRONMENTALLY PREFERRED ANTIMICROBIAL COMPOSITIONS

RELATED APPLICATIONS

This application is a continuation of U.S. patent application Ser. No. 14/500,473, titled "ENVIRONMENTALLY PREFERRED ANTIMICROBIAL COMPOSITIONS," filed Sep. 29, 2014, now U.S. Pat. No. 9,701,931, issued Jul. 11, 2017, which claims benefit of priority to U.S. Provisional Application No. 61/885,211 to Ryan Giffin Moore, titled "STABILIZING PERACID COMPOSITIONS," filed Oct. 1, 2013, and to U.S. Provisional Application No. 61/884,226 to Ryan Giffin Moore, titled "ENVIRONMENTALLY PREFERRED ANTIMICROBIAL COMPOSITION," filed Sep. 30, 2013, the subject matter of each of which is incorporated by reference in its entirety.

FIELD

This invention relates generally to antimicrobial compositions containing a peracid, and methods for disinfecting or sterilizing a hard surface by application of one of the antimicrobial compositions provided herein containing a peracid. In particular, the antimicrobial compositions provided herein are environmentally friendly compositions that can include a stable solution containing a peracid, such as peracetic acid (PAAH).

BACKGROUND

Disinfecting or sanitizing of hard surfaces, in the home, commercial and industrial settings, are necessary practices in order to promote and maintain good health. This is particularly true for the beverage, dairy, and food industries, in food packaging and preparation environments, and in service businesses. Failure to disinfect or sanitize equipment and other surfaces of contaminants can result in the growth of pathogenic microorganisms. Routine disinfection or sanitation is necessary to reduce microbial populations in order to protect consumers from potential health hazards associated with pathogenic microorganisms or toxins produced by such microorganisms.

Many existing antimicrobial compositions have drawbacks or undesirable properties that limit the ease of manufacture and/or use of the compositions. These include issues with availability and toxicity of ingredients, ease of use, efficacy, or having negative impacts on the items being treated, the individuals using the compositions, or on the environment. Examples of purported negative attributes or disadvantages of commonly used antimicrobial compositions are described in U.S. Pat. Appl. Publ. No. US20090074881 (2009). New antimicrobial compositions should comply with the increasing demand for safer, more environmentally friendly compositions.

Accordingly, there is a continuing need for antimicrobial compositions that exhibit improved stability, effective antimicrobial activity, and that also are eco-friendly or "green." The specific requirements for such compositions vary according to the intended application (e.g., disinfecting, sanitizing, sterilizing, etc.) and the governmental public health requirements associated with the intended application. Compositions having greater stability and antimicrobial activity while being environmentally friendly could help meet a substantial public health need, and one that is not adequately addressed by current commonly-used antimicrobial compositions.

SUMMARY

Provided are antimicrobial compositions that exhibit improved stability, enhanced antimicrobial efficacy, and that also are eco-friendly.

The antimicrobial compositions provided herein automatically adjust the pH of the solvent in which they are dissolved so that it first is alkaline, promoting the formation of a peracid, followed by a reduction of the pH to an acidic pH, stabilizing the in situ formed peracid.

The antimicrobial compositions provided herein include a hydrogen peroxide generator, a peracid catalyst, and a slow hydrolyzing acid, where the composition is a dry form, the ratio of the hydrogen peroxide generator to the peracetic acid catalyst is between 1.5:1 and 3:1 respectively, the slow hydrolyzing acid is present in an amount of at least about 10 wt %, and when 10 grams of the composition is dissolved in 90 grams of water to form a solution, the initial pH of the solution is about 8 or greater, and after 24 hours at room temperature the pH of the solution is about 7 or less. In some embodiments, the antimicrobial composition further includes a carboxylic acid. The antimicrobial compositions provided herein when dissolved in a solvent can produce a solution having an initial pH about 8 or greater, and after 24 hours at room temperature the pH of the solution is about 6.5 or less. The dry form can be a powder, flake, agglomerate, granule, tablet, capsule, pellet, puck, brick, briquette, block, unit dosage or composite.

The antimicrobial compositions can include a hydrogen peroxide generator that includes an alkali metal perborate, an alkali metal percarbonate, an alkali metal perphosphate, an alkali metal persilicate or an alkali metal persulfate or a combination thereof. In some embodiments, the hydrogen peroxide generator is sodium percarbonate, calcium peroxide, urea peroxide, sodium persulfate, potassium monopersulfate (Oxone®, DuPont™, Wilmington, Del.) or a combination thereof.

The antimicrobial compositions can include a peracid catalyst, which is an agent that contains an acetyl donor group or an acyl donor group or a combination thereof. The agent can contain an —O—C(O)CH$_3$ donor group, an —N—C(O)CH$_3$ donor group, an —O—C(O)R$^1$ donor group or an —N—C(O)R$^2$ donor group, wherein R$^1$ and R$^2$ each individually is C$_1$ to C$_{20}$ alkyl. The antimicrobial compositions can include a peracid catalyst selected from among monoacetin, diacetin, triacetin, glucose pentaacetate, lactose octaacetate, mannitol hexaacetate, sucrose octaacetate, N,N,N'N'-tetraacetylethylenediamine (TAED), N,N,N'N'-tetraacetylmethylene-diamine (TAMD), N-acetyl glycine, N-acetyl-methionine, 6-acetamidohexanoic acid, N-acetyl-L-cysteine, 4-acetamidophenol, N-acetyl-L-glutamine, and N,N',N",N'"-tetraacetyl glycoluril (TAGU). The antimicrobial compositions can include a peracid catalyst that is a peracetic acid catalyst. The peracetic acid catalyst can be TAED or TAMD.

The antimicrobial compositions can include a sugar acid lactone as a slow hydrolyzing acid. The antimicrobial compositions can include a sugar acid lactone selected from the group consisting of allohepturonolactone, allonolactone, alluronolactone, altrohepturonolactone, altronolactone, altruronolactone, arabinolactone, arabinuronolactone, galactohepturonolactone, galactonolactone, galacturonolactone, glucohepturonolactone, gluconolactone, glucuronolactone, gulohepturonolactone, gulonolactone, guluronolactone, idohepturonolactone, idonolactone, iduronolactone, lyxuronolactone, mannohepturonolactone, mannonolactone, mannuronolactone, ribonolactone, riburonolactone, talohepturonolactone, talonolactone, taluronolactone, xylonolactone and xyluronolactone and a combination thereof. The antimicrobial compositions can include a sugar acid lactone selected from the group consisting of a gluconolactone, a galactonolactone, a mannonolactone, a gulonolactone and a heptagluconolactone. The antimicrobial compositions can include a glucono-delta-lactone as a sugar acid lactone.

The antimicrobial compositions provided herein can include a hydrogen peroxide generator present in an amount of from about 10 wt % to about 60 wt %; a peracid acid catalyst present in an amount of from about 10 wt % to about 30 wt %; a slow hydrolyzing acid present in an amount of from about 5 wt % to about 60 wt %; and optionally a carboxylic acid present in an amount of from about 5 wt % to about 25 wt %.

The antimicrobial compositions provided herein can be in the form of a tablet, or a capsule, or a powder or an agglomerate. The antimicrobial compositions provided herein can be contained in a water soluble pouch. The water soluble pouch can include a water soluble polyvinyl alcohol. The pouch can include a plurality of compartments.

The antimicrobial compositions provided herein can include a protective layer. The protective polymer can include an acrylic, a sugar, a starch, a maltodextrin, a polyethylene glycol, or a film forming water soluble polymer or a combination thereof. When present, the film forming water soluble polymer can include a water soluble polyvinyl alcohol, polyvinylpyrrolidone, hydroxyethyl cellulose, hydroxypropylmethyl cellulose, methyl cellulose, carboxymethyl cellulose, xanthan gum, alginate, gellan gum, gelatin, or a modified starch or a combination of any of these.

The antimicrobial compositions provided herein can include a carboxylic acid. The carboxylic acid can be a straight chain aliphatic carboxylic acid or a branched chain aliphatic carboxylic acid. The carboxylic acid can be selected from the group consisting of acetic acid, citric acid, formic acid, gluconic acid, glycolic acid, lactic acid, maleic acid, malic acid, oxalic acid, succinic acid and tartaric acid.

The antimicrobial compositions provided herein can include an effervescent generator. The effervescent generator can include an alkali metal carbonate and an acid. The alkali metal carbonate can include an anhydrous potassium carbonate, a hydrated potassium carbonate, an anhydrous sodium carbonate, or a hydrated sodium carbonate or a combination thereof. The acid of the effervescent generator can be citric acid, ascorbic acid, aspartic acid, malic acid, adipic acid, tartaric acid, fumaric acid, succinic acid, sodium acid pyrophosphate, or lactic acid, or a combination thereof.

The antimicrobial compositions provided herein can include a color indicator. The color indicator changes color when the pH of the solution prepared by dissolving the antimicrobial composition in a solvent changes from alkaline to acidic. The color indicator can be present in an amount from at or about 0.005 wt % to about 1.0 wt % based on the weight of the composition. In some embodiments, antimicrobial compositions provided herein include sodium percarbonate as the hydrogen peroxide generator, TAED as the peracid catalyst, glucono-delta-lactone as the slow hydrolyzing acid, and citric acid as the carboxylic acid, when present.

Also provided are solutions that include from about 50 wt % to about 99.95 wt % of a solvent and from about 0.05 wt % to about 50 wt % of an antimicrobial composition provided herein. The solutions can be used as hard surface cleaners, hard surface disinfectants, hard surface sanitizer sprays, dishwasher sanitizers, laundry machine sanitizers, closed system sanitizers, and as dental, medical or surgical instrument soaking solutions for sanitizing or disinfecting the instruments. The solutions provided herein can include one or more additional components. The additional components can be selected from among an organic solvent, a surfactant, a buffering salt, a tablet lubricant, a fragrance, a colorant, a chelating agent, an enzyme, an acid, a carbonate, a bicarbonate, a phosphate, a wetting agent, a dispersing agent, a hydrotrope, a rheology control agent, a foam suppressant, a metal protectant, a corrosion inhibitor, an expanded percarbonate, a polyglycol, a polyalkylene glycol, a methoxypolyalkylene glycol, a polyglycol copolymer, a hexitol, a siloxane, a polysilane, a polysiloxane, a silicone detergent, sodium bisulfate and sulfamic acid and combinations thereof.

Preferred chelating agents include iminodisuccinic acid salts and methylglycinediacetic acid and combinations thereof. The surfactant can be a cationic, anionic, nonionic or amphoteric surfactant or a combination thereof. The enzyme can be selected from among a lipase, a protease, a peroxidase, an oxidase, an amylolytic enzyme, a cellulase, a polyesterase, a glucanase, an amylase, a glucoamylase, a glycosidase, a hemicellulase, a mannanase, a xylanase, a xyloglucanase, a pectinase, a β-glucosidase, or any combination thereof. The acid can be citric acid, ascorbic acid, aspartic acid, malic acid, adipic acid, tartaric acid, fumaric acid, succinic acid, sodium acid pyrophosphate, or lactic acid, or a combination thereof.

When present, the corrosion inhibitor can be a $C_4$-$C_{16}$ alkyl pyrrolidone, a $C_1$-$C_{18}$ alkylamine, a benzoate, an azole, an imidazole, a diazole, a triazole, an aromatic triazole, monosodium or monopotassium phosphate, disodium or dipotassium phosphate, sodium or potassium hexametaphosphate, hydroxyethylidine di-phosphonic acid, 8-hydroxyquinoline, orthophenylphenol, sarcosine or a sarcosinate or a combination thereof.

Also provided are hard surface sanitizer compositions, which include an antimicrobial composition provided herein, a carbonate or a bicarbonate or a combination thereof, and a solvent. Also provided are automatic dishwasher sanitizer compositions, which include an antimicrobial composition provided herein, and a carbonate or a bicarbonate or a combination thereof. The dishwasher sanitizer can further include a surfactant. The surfactant can be a cationic, anionic, nonionic or amphoteric surfactant or a combination thereof. The dishwasher sanitizer compositions can include an antimicrobial composition provided herein and a chelating agent. The chelating agent can be selected from among a iminodisuccinic acid salt, methylglycine diacetic acid trisodium salt, citric acid, diethylene triamine pentaacetic acid, ethylene diamine tetraacetic acid, ethylene glycol tetraacetic acid, glutamic acid diacetic acid, glutamic acid, and a combination thereof. Preferred chelating agents include an iminodisuccinic acid salt and methylglycinediacetic acid and a combination thereof.

Also provided are sanitizer spray compositions that include an antimicrobial composition provided herein, a solvent, and a bleach activator. The bleach activator can include an acylated alkylene diamine, benzoyl peroxide, benzoyl caprolactam, tetraacetyl glycouril, N-acylated hydantoine, hydrazine, triazole, hydratriazine, urazole, diketopiperazine, sulfurylamide, 6-nonyl-amino-6-oxoperoxy-caproic acid, cyanurate, a carboxylic acid anhydride, decanoyl-oxybenzenesulphonate sodium-acetoxy-benzene sulfonate, sodium-benzoyloxy benzene sulfonate, sodium-lauroyloxy-benzene sulfonate, sodium-isononanoyloxy benzene sulfonate, acylated sugar derivatives, pentaglucose, or nonanoyloxybenzene sulfonate, or a combination thereof.

Also provided are general purpose hard surface spray compositions that include an antimicrobial composition provided herein, a surfactant, a solvent, and a bleach activator. Also provided are clothing detergent compositions that include an antimicrobial composition provided herein and a surfactant. The clothing detergent compositions can include a carbonate or bicarbonate or a combination thereof. The clothing detergent compositions can include a bleaching agent, a bleach activator, an optical brightener, an anti-redeposition agent, a color, or a fragrance or any combination thereof. Also provided are garbage disposal cleaner compositions that include an antimicrobial composition provided herein, a carbonate or bicarbonate or a combination thereof, and a fragrance. Also provided are laundry machine sanitizer compositions that include an antimicrobial composition provided herein, a polyglycol, and a surfactant or a siloxane or a combination thereof.

Also provided are dental, medical or surgical instrument soaking solution compositions that include an antimicrobial composition provided herein and a corrosion inhibitor. The corrosion inhibitor can be selected from among a $C_4$-$C_{16}$ alkyl pyrrolidone, a $C_1$-$C_{18}$ alkylamine, a benzoate, an azole, an imidazole, a diazole, a triazole, an aromatic triazole, monosodium or monopotassium phosphate, disodium or dipotassium phosphate, sodium or potassium hexametaphosphate, hydroxyethylidine di-phosphonic acid, 8-hydroxyquinoline, orthophenylphenol, sarcosine, a sarcosinate and combinations thereof. The dental, medical or surgical instrument soaking solution compositions can include a chelating agent, a surfactant or an enzyme or a combination thereof.

Also provided are packaged systems that include an antimicrobial composition provided herein and a packaging material. The packaging material can be selected from the group consisting of glass, metal foil, treated metal foil, a metal foil pouch, plastic, plastic film, a plastic sheet, a blister pack, cardboard, a cardboard composite, paper and treated paper, and any combination thereof. The packaged system can include a container for dissolving the composition in a solvent or a receptacle for containing or dispensing the dissolved composition or both. The receptacle can be selected from the group consisting of a spray bottle, a sponge, a conventional hand sprayer container, an electric spray dispenser container, a bucket, a can, a drum, a towelette, a wipe, and a pad and any combination thereof.

Also provided are methods of disinfecting a surface. The methods include dissolving an antimicrobial composition provided herein in a solvent to form a disinfecting solution, and applying the disinfecting solution to the surface, resulting in the destruction of, or prevention of the growth of, a microbe on the surface. The solvent used to dissolve the antimicrobial composition can include water, an alcohol, an aldehyde, or a ketone or a combination thereof. The solvent can be the water in a laundry washing process or a dishwashing process. The disinfecting solution further can include a chelating agent, sodium bisulfate, a polyglycol, a hexitol, a siloxane, a polysilane, a polysiloxane, a silicone detergent, sodium carbonate, sodium gluconate, polyethylene glycol, an acrylic acid homopolymer, a surfactant, a bleaching agent, a bleach activator, an optical brightener, an anti-redeposition agent, a color, or a fragrance or any combination thereof. The disinfecting solution can be applied to the surface by spraying, wiping, immersion or direct application or any combination thereof. The disinfecting solution can be applied directly to a surface as a spray or fine mist. The disinfecting solution can applied via a woven or nonwoven substrate, a brush, a sponge, a wipe or a cleaning pad, or any combination thereof.

Also provided are articles of manufacture. The articles of manufacture include an antimicrobial composition provided herein and (a) a container suitable for containing the antimicrobial composition; or (b) a set of instructions for preparing a cleaning solution or disinfectant solution by dissolving the antimicrobial composition in a solvent; or (c) a set of instructions for storing the antimicrobial composition; or (d) a material safety data sheet; or (e) a dispenser or applicator for a solution prepared by dissolution of the antimicrobial composition; or (f) any combination of two or more of (a), (b), (c), (d) and (e). The container can be made of or contain glass, acrylonitrile butadiene styrene (ABS), high impact polystyrene, polycarbonate, high density polyethylene, low density polyethylene, high density polypropylene, low density polypropylene, polyethylene terephthalate, polyethylene terephthalate glycol and polyvinylchloride and combinations thereof. The containers can include a barrier film to increase storage stability.

DETAILED DESCRIPTION

Outline
A. Definitions
B. Antimicrobial Compositions
C. Components of Eco-Friendly Antimicrobial Compositions
  1. Hydrogen Peroxide Generator
  2. Peracid Catalyst
  3. Slow Hydrolyzing Acid
  4. Carboxylic acid
  5. Forms
  6. Effervescent Formulations
  7. Protective Layer
D. Methods of Preparation
  1. Composition Preparation
  2. Agglomerate Preparation
  3. Tablet Preparation
E. Packaged Systems
F. Articles of manufacture
G. Applications
H. Examples
A. Definitions Unless defined otherwise, all technical and scientific terms used herein have the same meaning as is commonly understood by one of skill in the art to which the inventions belong. All patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, the singular forms "a," "an" and "the" include plural referents unless the context clearly dictates otherwise.

As used herein, ranges and amounts can be expressed as "about" a particular value or range. "About" also includes the exact amount. Hence "about 5 percent" means "about 5 percent" and also "5 percent." "About" means within typical experimental error for the application or purpose intended.

As used herein, "optional" or "optionally" means that the subsequently described event or circumstance does or does not occur, and that the description includes instances where the event or circumstance occurs and instances where it does not. For example, an optional component in a system means that the component may be present or may not be present in the system.

As used herein, "weight percent" or "wt %" refers to the concentration of a substance as the weight of that substance divided by the total weight of the composition and multiplied by 100.

As used herein, a "hydrogen peroxide generator" refers to a chemical compound that produces hydrogen peroxide or hydroxyl radical when dissolved in a solvent containing water.

As used herein, "peracid" refers to a peroxyacid (or percarboxylic acid or peroxycarboxylic acid) having the general formula $R^3(CO_3H)_n$, where $R^3$ can be saturated or unsaturated as well as substituted or unsubstituted and selected from among alkyl, arylalkyl, cycloalkyl, aromatic, heterocyclic, ester and alkyl ester groups; and n is one, two, or three. Exemplary peracids include peracetic acid (PAAH, peroxyacetic acid), perbenzoic acid (peroxybenzoic acid) and substituted forms of perbenzoic acid; di-peroxymalonic acid, di-peroxysuccinic acid, di-peroxyglutaric acid, di-peroxyadipic acid; all isomeric forms of each of peroxypropionic acid, peroxybutanoic acid, peroxyhexanoic acid, peroxydodecanoic acid, and peroxylactic acid. PAAH is a representative peracid, and compositions and methods provided herein that are exemplified with PAAH can be practiced in general with any one or combination of peracids.

As used herein a "peracid catalyst" refers to a compound that reacts with hydrogen peroxide or peroxide ions to form a peracid. The peracid catalyst can include any compound that contains an acetyl or acyl donor group for reacting with hydrogen peroxide or peroxide ions to form a peracid.

As used herein, "peracetic acid" refers to peroxyacetic acid, which is a peroxycarboxylic acid having the formula $CH_3COOOH$.

As used herein, a "peracetic acid catalyst" refers to a compound that reacts with hydrogen peroxide to form a peracetic acid.

As used herein, a "slow hydrolyzing acid" refers to an acid that slowly hydrolyzes with time to provide an additional carboxylic acid moiety, thereby further reducing the pH of a solution in which it is dissolved. Exemplary slow hydrolyzing acids are acids containing a lactone, which hydrolyzes over time, such as a sugar acid lactone.

As used herein, "surfactant" refers to surface active molecules that absorb at the air/water, oil/water and/or oil/water interfaces, substantially reducing their surface energy. The term "detergent" is often used interchangeably with the term "surfactant." Surfactants generally are classified depending on the charge of the surface active moiety, and can be categorized as cationic, anionic, nonionic and amphoteric surfactants.

As used herein, "effervescent generator" refers to a composition that gives off gas (e.g., carbon dioxide) bubbles when placed in an aqueous liquid.

As used herein, a "protective layer" refers to a layer that coats a surface in order to protect the surface from an influence of physical or chemical action applied from the surroundings.

As used herein, a "composite" refers to a mixture of two or more different ingredients in which the ingredients do not dissolve or merge completely, but which forms a substantially homogeneous material (i.e., a material without laminate structure or a composition gradient).

As used herein, a "layered compression" refers to composition containing two or more different ingredients in which the ingredients have a laminate structure or a composition gradient or both. The composition is formed by compressing the ingredients into a dry form, and can include multiple layers.

As used herein, an "agglomerate" refers to a material obtained by mixing two or more materials and agglomerating the resulting mixture. Such agglomeration is carried out using any of various known devices, examples of which include presses such as briquetting presses (e.g., cylinder briquette press, roller briquette press, ring roller briquette press), and also extruders and tumbling granulators (e.g., pan pelletizer, drum pelletizer). The shape of the agglomerate is not subject to any particular limitation. Any of various shapes may be used, such as blocky, granular, briquette-like, pellet-like or rodlike.

As used herein, "water soluble" refers to a compound that can be dissolved in water at a concentration of more than 1 wt %.

As used herein, "pouch" refers to a hollow sealable container.

As used herein, "water soluble or water dispersible protective pouch" refers to a pouch that at least partially dissolves in water or disperses in 1 liter of water at 21° C. within 10 minutes either with agitation or without agitation to allow for egress of the contents of the pouch into the surrounding water.

As used herein, a "stabilized peracid composition" has an enhanced stability, e.g., exhibits an increased shelf life or retains a higher level of peracid over a given period of time, when compared to a peracid composition prepared by standard methods.

As used herein, "stable" refers to the retention of at least 80% of the initial equilibrium peracid level for at least six months after storage at room temperature.

As used herein, "disinfect" refers to the process of destruction of, or prevention of the growth of, biological contaminants, which can include microbes.

As used herein, "disinfectant" refers to an agent that disinfects by destroying, neutralizing, or inhibiting the growth of biological contaminants, which can include microbes.

As used herein, "sanitary" means of or relating to the restoration or preservation of health, typically by removing, preventing or controlling an agent that may be injurious to health, such as microbes.

As used herein, "sanitize" means to make sanitary.

As used herein, "sanitizer" refers to an agent that sanitizes.

As used herein, "microbes" refers to any organism that is a member of the phylogenetic domains bacteria and archaea, as well as unicellular and filamentous fungi (such as yeasts and molds), unicellular and filamentous algae, unicellular and multicellular parasites, and viruses. Exemplary microbes include bacteria, e.g., Gram-positive and Gram-negative cocci, Gram-positive and Gram-negative straight, curved, helical or vibroid and branched rods, sheathed bacteria, sulfur-oxidizing bacteria, sulfur or sulfate-reducing bacteria; spirochetes; actinomycetes and related genera; myxobacteria; mycoplasmas; rickettsias; chlamydias; cyanobacteria; archea; fungi; parasites; viruses; and algae.

As used herein, "eco-friendly" means not harmful to, or having minimal negative impact on, the environment.

As used herein, a "solid" refers to a hardened composition that does not flow perceptibly and that substantially retains its shape under moderate stress, pressure or gravity.

As used herein, "antimicrobial activity" refers to partial or complete inhibition of growth of a microbe, or causing lysis of a microbe, or both. A sanitizer and a disinfectant are exemplary agents that have antimicrobial activity.

As used herein, "antimicrobial composition" is a composition that partially or completely inhibits growth of a microbe, or causes lysis of a microbe, or both.

As used herein, "acidic range" means a pH less than 7.

As used herein, "metal protector" refers to a material, substance, composition, or compound that protects a metal from its environment.

As used herein, "corrosion inhibitor" refers to a material, substance, composition, or compound that reduces, decreases, diminishes, lowers, or minimizes the corrosion of a metal or metal alloy from the surface of a metal component in the presence of metal corroding agent.

As used herein, "room temperature" means an ambient temperature in the range of from about 20° C. to about 25° C. (generally having an average of about 21° C.).

B. Antimicrobial Compositions

Many of the antimicrobial compositions in use can have a negative impact on the environment. For example, some halogenated phenolics can present environmental concerns because they are difficult to degrade. Some antimicrobial compounds, such as hypochlorite, can react with many organic materials, which can result in the production of carcinogenic compounds. Some surfactants used as antimicrobials can be toxic to aquatic life. Some antimicrobials in use are not biodegradable and can be persistent in the environment.

The compositions provided herein have antimicrobial properties and are "green" or eco-friendly. Eco-friendly compositions include those recognized to have minimal negative impact on the environment. For example, the United States Environmental Protection Agency's Design for the Environment Antimicrobial Pesticide program allows for special labeling of compositions that can meet certain requirements. These include that the product is unlikely to cause developmental, mutagenic, neurotoxic or reproductive harm, does not require the use of EPA-mandated personal protective equipment, and has no unreasonable or unresolved adverse effects reported. Such products must demonstrate antimicrobial activity on hard, non-porous surfaces.

The compositions and methods provided herein are environmentally safe. The compositions provided herein have superior or equal antimicrobial performance when compared to other standard antimicrobial agents, with the added benefits of being particularly "green" or eco-friendly compositions, and the ability to be formulated as a stable dry powder or tablet that can be reconstituted, which further decreases any negative environmental impact. The composition provided herein, including the dry powder or tablet forms of the compositions and the diluted liquid forms prepared by dissolving the dry powder or tablets forms of the composition in a solvent, can be stored, before or after dilution, and maintain stability for a prolonged period of time, which is another advantageous outcome of the present technology.

The antimicrobial compositions provided herein produce a peracid, such as a peracetic acid (PAAH). The antimicrobial compositions provided herein also can be prepared in combination with other ingredients. The present invention addresses the need for an antimicrobial composition that is environmentally safe, stable, and that can be applied effectively to hard surfaces. The antimicrobial composition provided herein can be used to decontaminate (e.g., disinfect or sterilize) solid surfaces contaminated with bacteria, bacterial spores and/or fungi. The compositions provided herein containing a peracid provide a stable, cost effective technology that is reliable and easy to use.

PAAH is one of the very few antimicrobial chemistries that is acceptable under the current US EPA Design for the Environment Antimicrobial program for use in closed systems, such as dishwashers and washing machines. This means that using PAAH as a hard surface sanitizer or disinfectant can be environmentally preferred over other antimicrobials, such as halogens or cationic detergents. Previously, producing PAAH dissolved in solution would require the resulting solution to be used immediately before degradation of the PAAH due to an alkaline pH, or an excess of reactants to produce enough PAAH to be an effective sanitizer or disinfectant and/or very acidic conditions were required to maintain stable PAAH so that the solution could be used at a later date. The compositions and methods provided herein avoid the degradation of peracid in solution.

The antimicrobial compositions and methods provided herein include a peracid compound as a catalyst. Peracid compounds, particularly PAAH, function very well as antimicrobial compounds, and are used as sanitizers, disinfectants, and deodorizers (e.g., see U.S. Pat. No. 8,568,861). In fact, several hospital grade disinfectants have been using PAAH as a hard surface disinfectant and cold sterilizer for more than a decade. The industry has several methods to produce functional PAAH solutions for use in the marketplace. Most of these formulas require strong acid environments and stabilizers to keep the PAAH chemistry from degrading.

The antimicrobial compositions and methods provided herein include peracid compounds but avoid the degradation of peracid in solution. In one embodiment, the antimicrobial compositions include tetraacetyl ethylenediamine (TAED) as a hydrogen peroxide catalyst. TAED is known in the dry chemical industry to be useful for making powder and compressed tablet compositions because TAED is stable in dry form and compatible with the peroxygen chemistries needed to make PAAH in solution. One example of how TAED has been used in the marketplace is the use of TAED with sodium perborate, which allows the sodium perborate to release its hydrogen peroxide in cold water applications. Another example is the use of TAED with sodium percarbonate to enhance the hydrogen peroxide chemistry to PAAH which allows for a more enhanced peroxygen chemistry in cold water applications Both of these chemistries are important to the laundry category as color safe bleach technologies. Color safe bleach technologies are ones that do not use chlorine bleach technologies.

Conventional peracids have inherent disadvantages, one of which is limited storage stability. The shelf life of peracid products is commonly defined by the peracid storage stability. A desirable shelf life often requires a 80% or higher retention of the initial equilibrium peracid level in the product for at least 6 months after storage at ambient temperature. The industry has several methods to produce functionally stable PAAH solutions, most of which require a strong acidic pH environment and stabilizers to stabilize the PAAH for long term shelf storage. Peracid products that have an enhanced storage stability/shelf life would reduce the number of products being discarded due to peracid degradation, thereby reducing waste.

As described herein, it has been found that one way to avoid the degradation of peracid in solution is to provide PAAH generation chemistry in a stable dry form that does not release the peracid until the dry form is dissolved in a solvent, such as water, resulting in the in situ formation of a peracid solution that can be used as an antimicrobial. For example, a dry hydrogen peroxide source can be combined with TAED and delivered as a powder or tablet. Each component will remain shelf stable for long periods of time. The PAAH can be produced once the powder or tablet is dissolved in a solvent, such as water.

An inherent pH problem exists with PAAH generation chemistry. TAED has a pKa of 8. This means that in order for 50% of the TAED to disassociate in solution to be available as a catalyst to make PAAH, the pH has to be at least 8.0. The pH has to go even higher (become more alkaline) in order to get more TAED disassociation and thus a higher ppm of PAAH in solution. Therefore, after the TAED disassociates and makes PAAH, the alkaline solution would destabilize and destroy the PAAH.

As explained above, the pH ideally is in the acid range to keep the produced PAAH stable. Addition of a typical acid, such as an inorganic acid or a carboxylic acid, to the composition results in too rapid of a pH drop, interfering with the effective creation of the PAAH (which requires alkaline conditions for formation). The art discusses reduction of pH in an aqueous solution by user introduction or injection of an acid agent from an external source (e.g., see U.S. Pat. No. 5,505,740 (Kong et al. (1996)). Manual adjustment of the pH by a consumer to an acidic pH is inconvenient, and it would be undesirable to require an end-user to adjust the pH from alkaline to acidic, such as by handling acidic chemicals, in order to obtain a stable product.

It has been discovered that including a slow hydrolyzing acid in the composition results in an automatic reduction in the pH to an acidic range over time after formation of the PAAH, resulting in a solution (and its PAAH) that is stable. Accordingly, provided herein is a composition that includes a slow hydrolyzing acid, which provides a time delayed modulation of the pH of a solution resulting when the composition is dissolved in a solvent. The compositions provided herein maximize the production of PAAH at an alkaline pH followed by an automatic reduction in the pH over time to an acidic pH, stabilizing the PAAH in solution. In some applications, the pH is reduced to less than 7 within 24 hours at room temperature. In some applications, the pH is about 6.5 or less after 24 hours. In some applications, the pH is reduced to a pH of about 6 or less within 24 hours at room temperature.

The compositions provided herein address a market need for an environmentally preferred antimicrobial that is stable in dry form. The compositions provided herein maximize PAAH creation when dissolved in a solvent, e.g. water, producing a pH above 8.0, and then stabilize the PAAH in solution long term by automatically reducing the pH to the acid range over time.

In particular, provided are compositions in dry form that include a PAAH catalyst in combination with a hydrogen peroxide generator and a slow hydrolyzing acid. The composition, when dissolved in a solvent, results in the formation of a stable solution containing PAAH. In one embodiment, the composition includes a dry hydrogen peroxide source, such as a percarbonate or peroxide or combinations thereof, with a peracetic acid catalyst, such as TAED and a slow hydrolyzing acid, such as a sugar acid lactone, and the composition is provided in dry form, such as a powder, flake, agglomerate, granule, tablet, capsule, pellet, puck, brick, briquette, block, unit dosage, layered compression or composite. The dry forms of the compositions are shelf stable for long periods of time, and readily will produce a peracid, such as PAAH, once dissolved in a solvent, such as water. The compositions provided herein are environmentally preferred antimicrobial compositions that are stable in dry form, that can maximize peracid (e.g., PAAH) creation when initially dissolved in solution, resulting in a solution having an initial pH of at or about 8.0 or greater, and that automatically over time reduces the pH of the solution to the acid range (e.g., a pH less than 7), stabilizing the peracid (e.g., PAAH) in solution long term.

The antimicrobial compositions provided herein produce a peracid in solution in an amount from about 100 ppm to about 1,000 ppm. In some embodiments, the antimicrobial compositions provided herein produce PAAH in solution in an amount from about 100 ppm to about 1,000 ppm. In some embodiments, the amount of PAAH produced is from about 100 ppm to about 500 ppm. In some embodiments, the amount of PAAH produced is at least 100 ppm, or at least 150 ppm, or at least 200 ppm, or at least 250 ppm, or at least 300 ppm, or at least 350 ppm, or at least 400 ppm, or at least 450 ppm, or at least 500 ppm.

Sodium percarbonate is a good example of an alkaline, hydrogen peroxide source capable of making the solution pH rise to at or about 8.0 or higher to maximize peracid creation, (e.g., PAAH from TAED) Sugar acid lactones are good examples of a slow hydrolyzing acid. If a typical organic acid, such as a carboxylic acid, is used instead of the sugar acid lactone, an immediate drop in pH occurs upon dissolution, interfering with the effective creation of the peracid. Sugar acid lactones have a mild acidic pH when first dissolved, and then reduce the pH of the solution to a more strongly acidic range. Some sugar acid lactones in solution by themselves can result in a final solution pH as low as a pH of 2.5 when fully hydrolyzed to its acid form. A sugar acid lactone can take hours or days to fully hydrolyze into its more acidic form. This delay in becoming an acid is used in the compositions provided herein to stabilize in situ produced peracids. For example, when sodium percarbonate and TAED are mixed with a sugar acid lactone, the composition produces a solution having a pH of at or about 8 or greater initially and maintains the alkaline pH for some time, e.g., for several minutes to several hours, depending on the formulation, giving the solution enough time to maximize PAAH creation. This results in a solution containing sufficiently high ppm of PAAH to be an effective sanitizer or disinfectant. As the sugar acid lactone slowly hydrolyzes into its acid form, it lowers the solution pH to the acid range and therefore stabilizes the PAAH that was originally created in the solution under alkaline conditions. The pH modulation using the compositions provided herein is automatic and does not require any user intervention, such as addition of any chemicals by the user.

The antimicrobial compositions provided herein can be maintained in their dry form until ready for use. The dry form, e.g., agglomerate, granule, flake, tablet, capsule, pellet, puck, brick, briquette, block, layered compression or composite, can include a polymer coating as a protective layer. The polymer coating can be applied to the surface of the solid form of the antimicrobial composition. The protective layer can be in the form of a film, packet, pouch, sheath or envelope that surrounds, partially or completely, the solid form of the antimicrobial composition.

In their dry form, the antimicrobial compositions provided herein are substantially stable at room temperature for a year or more. When dissolved in a solvent, the antimicrobial compositions provided herein result in in situ formation of a peracid and automatically adjust the initially alkaline pH of the solution to an acidic pH over time, generally within about 24 hours. In some applications, the resulting solutions containing the antimicrobial compositions provided herein retain at least about 50% of the initial equilibrium peracid level for about 1 year at room temperature. In some applications, the resulting solutions containing the antimicrobial compositions provided herein retain at least about 80% of the initial equilibrium peracid level for about 1 year at room temperature.

C. Components Of Eco-friendly Antimicrobial Compositions

Provided herein are eco-friendly, environmentally acceptable antimicrobial compositions that are stable in dry form. The compositions maximize peracid (e.g., PAAH) creation when initially dissolved in an aqueous solvent because the resulting solution has an initial pH of at or above 8.0. The composition then automatically modifies the solution pH to an acidic pH (e.g., less than 7, preferably at or less than 6.5) after 24 hours at room temperature, stabilizing the peracid (e.g., PAAH) in solution long term. The antimicrobial compositions provided herein include a hydrogen peroxide generator, a peracetic acid catalyst, and a slow hydrolyzing acid, where the ratio of the hydrogen peroxide generator to the peracetic acid catalyst is between 1.5:1 and 3:1, and when dissolved in a solvent, the initial pH of the solution is alkaline and after 24 hours the pH of the solution is acidic. In some embodiments, the antimicrobial compositions provided herein include a hydrogen peroxide generator, a peracetic acid catalyst, a slow hydrolyzing acid, and a carboxylic acid.

The environmentally acceptable antimicrobial compositions provided herein can be dissolved in any solvent. Exemplary solvents include water, an alcohol, an aldehyde, and a ketone and combinations thereof. For many applications, the solvent includes water.

The antimicrobial composition provided herein can include one or more additional components. Exemplary additional components include, e.g., organic solvents, surfactants, a buffering salt, tablet lubricants, fragrances, colorants, chelants (e.g., iminodisuccinic acid salts (available as Baypure® CX 100 from Lanxess Deutchland GmBH, Leverkusen Germany) and methylglycinediacetic acid (Trilon® M from BASF, Florham Park, N.J.)), enzymes, acids, carbonates or bicarbonates, phosphates, wetting agents, dispersing agents, hydrotropes, rheology control agents, foam suppressants, metal protectants, corrosion inhibitors, and other functional additives. In some applications, the formulation includes an expanded percarbonate as described in U.S. Pat. Appln. Pub. No. US2012/0219513. In some applications, the formulation can include a sodium perborate or an expanded sodium perborate. In some applications, the cleaning or disinfecting formulation contains an acid selected from among acetic, adipic, azelaic, citric, fumaric, glutaric, maleic, malonic, oxalic, pimelic, suberic, sebacic, and succinic acid and combinations thereof. In some applications, the acid is selected from among acetic acid, citric acid, malic acid, adipic acid and oxalic acid. In some applications, the formulation includes a solid acetic acid as described in U.S. Pat. Appln. Pub. No. US2012/0208740. These other ingredients can be present in the range of about 0.05% to 75%, or in the range of about 0.25% to 60%, or in the range of about 0.5% to 50%, or in the range of about 0.75% to 40% based on the weight of the tablet. In some applications, the tablet includes an effervescent generator that allows the dry form of the antimicrobial composition provided herein to effervesce. In some embodiments, the antimicrobial compositions provided herein are free of EDTA. In some embodiments, there is no calcium salt of EDTA or magnesium salt of EDTA in the composition. In some embodiments, the antimicrobial compositions provided herein are free of borates, boric acid or perborates.

The antimicrobial compositions provided herein can include a surfactant. The antimicrobial compositions provided herein can include a fragrance, alone or in combination with an additional component, such as a surfactant, carbonate, bicarbonate, acid or effervescent generator or combinations thereof. The antimicrobial compositions provided herein can include a carbonate or bicarbonate or a combination thereof, alone or in combination with an additional component, such as a surfactant, fragrance, acid or effervescent generator or a combination thereof. The antimicrobial compositions provided herein can include a chelant, alone or in combination with an additional component. The antimicrobial compositions provided herein can include a buffer, alone or in combination with an additional component. The antimicrobial compositions provided herein can include a phosphate, alone or in combination with an additional component. The antimicrobial compositions provided herein can include a wetting agent or a dispersing agent or both, alone or in combination with an additional component. The antimicrobial compositions provided herein can include an acetate, alone or in combination with an additional component. The antimicrobial compositions provided herein can include an enzyme, alone or in combination with an additional component. The enzyme can be a lipase, a protease, a peroxidase, an oxidase, an amylolytic enzyme, a cellulase, a polyesterase, a glucanase, an amylase, a glucoamylase, a glycosidase, a hemicellulase, a mannanase, a xylanase, a xyloglucanase, a pectinase, a β-glucosidase, or any combination thereof.

1. Hydrogen Peroxide Generator

The antimicrobial compositions provided herein include a hydrogen peroxide generator. Any hydrogen peroxide generator known in the art can be used. Exemplary hydrogen peroxide generators include, but are not limited to, organic peroxides such as carbamide peroxide and urea peroxide, peroxide complexes, and inorganic persalts such as the alkali metal perborates, percarbonates, perphosphates, persilicates and persulfates. In some embodiments, preferred hydrogen peroxide generators are the alkali metal percarbonates. In some embodiments, preferred hydrogen peroxide generators include sodium percarbonate, calcium peroxide, magnesium peroxide, urea peroxide, sodium persulfate, potassium monopersulfate (Oxone®, DuPont™, Wilmington, Del.) or combinations thereof. In some embodiments, a preferred hydrogen peroxide generator is sodium percarbonate.

The hydrogen peroxide generator can be present in the compositions provided herein in an amount from about 1 wt % to about 99 wt %. For example, the hydrogen peroxide generator can be present in an amount from about 1 wt % to about 20 wt %, or from about 5 wt % to about 50 wt %, or from about 10 wt % to about 80 wt %, or from or from about 15 wt % to about 95 wt %, or from about 20 wt % to about 70 wt %. It is to be understood that all values and ranges between these values and ranges are encompassed by the compositions and methods provided herein.

2. Peracid Catalyst

The antimicrobial compositions provided herein include a peracid catalyst. The peracid catalyst can include any agent that contains an acetyl or acyl donor group for reacting with hydrogen peroxide or peroxide ions to form a solution that includes a peracid. In some embodiments, the peracid catalyst is a peracetic acid catalyst that contains an acetyl or acyl donor group for reacting with hydrogen peroxide or peroxide ions to form a peracetic acid. Exemplary peracids include peracetic acid (PAAH, peroxyacetic acid), perbenzoic acid (peroxybenzoic acid) and substituted forms of perbenzoic acid; di-peroxymalonic acid, di-peroxysuccinic acid, di-peroxyglutaric acid, di-peroxyadipic acid; all isomeric forms of each of peroxypropionic acid, peroxybutanoic acid, peroxyhexanoic acid, peroxydodecanoic acid, and peroxylactic acid. PAAH is a representative peracid, and compositions and methods provided herein that are exemplified with PAAH can be practiced in general with any one or combination of peracids. Examples of peracid catalysts include O-acetyl (—O—C(O)CH$_3$) donors, N-acetyl (—N—C(O)CH$_3$) donors, O-acyl (—O—C(O)R') donors and N-acyl (—N—C(O)R") donors, where R and R' are C$_1$ to C$_{20}$ alkyl substituents. Examples of 0-acetyl donors include monoacetin, diacetin, triacetin, glucose pentaacetate, lactose octaacetate, mannitol hexaacetate and sucrose octaacetate. Examples of N-acetyl donors include N,N,N'N'-tetraacetylethylenediamine (TAED), N,N,N'N'-tetraacetylmethylene-diamine (TAMD), N-acetyl glycine, N-acetyl-methionine, 6-acetamidohexanoic acid, N-acetyl-L-cysteine, 4-acetamidophenol, N-acetyl-L-glutamine, and N,N',N'',N'''-tetraacetyl glycoluril (TAGU). In some embodiments, it is preferred that the peracid catalyst, e.g. peracetic acid catalyst, be a solid at room temperature. In some embodiments, a peracid catalyst, e.g., peracetic acid catalyst, having a pK$_a$ of about 8 or greater is selected. In some embodiments, a peracid catalyst having a pKa in the range from about 7 to about 11, or from about 8 to about 10, is selected. In some embodiments, the preferred peracetic acid catalyst is TAED or TAMD or a combination thereof. Many of the known bleach activators can function as peracid catalysts. Bleach activators are described in U.S. Pat. Nos. 4,412,934; 4,634,551; 4,915,854; 4,966,723; 6,080,710; and 7,235,252. Exemplary bleach activators include an acylated alkylene diamine, benzoyl peroxide, benzoyl caprolactam, tetraacetyl glycouril, N-acylated hydantoine, hydrazine, triazole, hydratriazine, urazole, di-ketopiperazine, sulfurylamide, 6-nonyl-amino-6-oxoperoxy-caproic acid, cyanurate, a carboxylic acid anhydride, decanoyl-oxybenzenesulphonate sodium-acetoxy-benzene sulfonate, sodium-benzoyloxy benzene sulfonate, sodium-lauroyloxy-benzene sulfonate, sodium-isononanoyloxy benzene sulfonate, acylated sugar derivatives, pentaglucose, nonanoyloxybenzene sulfonate, and combinations thereof. In some embodiments, the antimicrobial compositions include TAED or TAMD or a combination thereof as the peracetic acid catalyst, and sodium percarbonate as the hydrogen peroxide generator.

The peracid catalyst, e.g. a peracetic acid catalyst, can be present in the compositions provided herein in an amount from about 1 wt % to about 50 wt %. For example, the peracid catalyst can be present in an amount of from about 1 wt % to about 10 wt %, or from about 2 wt % to about 20 wt %, or from about 5 wt % to about 25 wt %, or from about 10 wt % to about 40 wt %, or from or from about 15 wt % to about 35 wt %, or from about 20 wt % to about 50 wt %. It is to be understood that all values and ranges between these values and ranges are encompassed by the compositions and methods provided herein.

The ratio of hydrogen peroxide generator to peracid catalyst, e.g. peracetic acid catalyst, is in a range of from about 1.5:1 to about 3:1. For example, the ratio of hydrogen peroxide generator to peracid or peracetic acid catalyst can be 1.5:1, 1.55:1, 1.6:1, 1.65:1, 1.7:1, 1.75:1, 1.8:1, 1.85:1, 1.9:1, 1.95:1, 2:1, 2.05:1, 2.1:1, 2.15:1, 2.2:1, 2.25:1, 2.3:1, 2.35:1, 2.4:1, 2.45:1, 2.5:1, 2.55:1, 2.6:1, 2.65:1, 2.7:1, 2.75:1, 2.8:1, 2.85:1, 2.9:1, 2.95:1, or 3:1.

In some embodiments, the peracid catalyst can be separated from the hydrogen peroxide generator in the composition. The separation can be achieved, e.g., by using a polymer coating on the particles of the peracid catalyst and the hydrogen peroxide generator in the composition. The same or different polymer coating can be applied to the particles of the peracid catalyst and the hydrogen peroxide generator in the composition. Suitable coating materials include adipic acid, azelaic acid, glutaric acid, malonic acid, oxalic acid, pimelic acid, sebacic acid, suberic acid, succinic acid, undecanedioic acid, dodecanedioic acid, tridecanedioic acid, hydroxypropyl cellulose, hydroxypropyl methylcellulose (e.g., Opadry® coating), polyvinylacetate, hydroxyethyl cellulose, methylhydroxyethyl cellulose, methyl cellulose, ethyl cellulose (e.g., Surelease® coating), cellulose acetate, sodium carboxymethyl cellulose, polymers and copolymers of acrylic acid and methacrylic acid and esters thereof (e.g., Eudragit® RL, Eudragit® RS, Eudragit® L100, Eudragit® S100, Eudragit® NE), starch, modified starch, matlodextrin, a wax, gum arabic, shellac, water soluble polyvinyl alcohol, polyalkylene glycols, acrylic polymer, such as sodium polyacrylate, or polyvinylpyrrolidone, or combinations thereof. In some embodiments, the polymer coating is or contains a water soluble polyvinyl alcohol or a polyalkylene glycol. Exemplary polyalkylene glycols include polyethylene glycol and polypropylene glycol. When used, the molecular weight of the polyalkylene glycol can be selected to be in the range of about 400 to about 8000. In some embodiments, the peracid catalyst can be separated from the hydrogen peroxide generator in the composition by enclosing particles or tablets of each separately in a film, packet, pouch, sheath or envelope that surrounds and separates the particles or tablets of the peracid catalyst from the particles or tablets of the hydrogen peroxide generator. The film, packet, pouch, sheath or envelope can contain or be made of a material that dissolves or disperses rapidly when exposed to an aqueous solvent, thereby releasing the contained particles or tablets into to the aqueous solvent.

3. Slow Hydrolyzing Acid

The antimicrobial compositions provided herein include a slow hydrolyzing acid. After peracid has been formed in the solution by the reaction between the hydrogen peroxide generator and the peracid catalyst, the slow hydrolyzing acid reduces the pH of the solution. Slow hydrolyzing acid can be present in the compositions provided herein in an amount from about 0.5 wt % to about 60 wt %. For example, the slow hydrolyzing acid can be present in an amount of from about 1 wt % to about 10 wt %, or from about 2 wt % to about 20 wt %, or from about 5 wt % to about 25 wt %, or from about 10 wt % to about 40 wt %, or from or from about 15 wt % to about 35 wt %, or from about 5 wt % to about 50 wt %, or from about 12 wt % to about 60 wt %. It is to be understood that all values and ranges between these values and ranges are encompassed by the compositions and methods provided herein An exemplary slow hydrolyzing acid is a sugar acid lactone. The sugar acid lactones are acids that slowly hydrolyze to provide an additional carboxylic acid moiety, thereby reducing the pH of a solution in which they are dissolved. Any sugar acid lactone can be used as a slow hydrolyzing acid to act at the slow hydrolyzing acid in the compositions provided herein. Exemplary sugar acid lactones include the alpha and beta forms of allohepturonolactone, allonolactone, alluronolactone, altrohepturonolactone, altronolactone, altruronolactone, arabinolactone, arabinuronolactone, galachepturono-lactone, galactonolactone, gal acturonolactone, glucohepturonolactone, gluconolactone, glucuronolactone, gulohepturonolactone, gulonolactone, guluronolactone, idohepturonolactone, idonolactone, iduronolactone, lyxuronolactone, mannohepturonolactone, mannonolactone, mannuronolactone, ribonolactone, ribu-ronolactone, talohepturonolactone, talonolactone, taluronolactone, xylonolactone and xyluronolactone.

In some embodiments, the sugar acid lactone is selected from among the group consisting of a gluconolactone, a galactonolactone, a mannonolactone, a gulonolactone and a heptagluconolactone and combinations thereof. In some embodiments, the sugar acid lactone is selected from among D-glucono-delta-lactone [CAS-No. 90-80-2], D-galactono-gamma-lactone [CAS-No. 2782-07-2], L-mannono-gamma-lactone [CAS-No. 22430-23-5], D-gulono-gamma-lactone [CAS-No. 6322-07-2], L-gulono-gamma-lactone [CAS-No. 1128-23-0], α-D-heptaglucono-gamma-lactone [CAS-No. 60046-25-5] and combinations thereof. In some embodiments, the slow hydrolyzing acid is a sugar acid delta lactone. In some embodiments, the slow hydrolyzing acid is D-glucono-[delta]-lactone [CAS-No. 90-80-2]. In some embodiments, the slow hydrolyzing acid is a glucono-delta-lactone, delta-gluconolactone, D-glucofuranurono-6,3-lactone, or glucurolactone or a combination thereof. In some embodiments, the slow hydrolyzing acid is a gluconolactone, a galactonolactone, a mannonolactone, a gulonolactone, a glucono-delta-lactone or a heptagluconolactone or a combination thereof. In some embodiments, the antimicrobial compositions include TAED or TAMD or a combination thereof as the peracetic acid catalyst, sodium percarbonate as the hydrogen peroxide generator, and glucono-delta-lactone as the slow hydrolyzing acid.

The sugar acid lactones are commercially available or can be synthesized using known methods. For example, many alduronic acids form intramolecular lactones by removing one mole of water between the carboxyl group and one hydroxyl group. These internal esters of alduronic acids are spontaneously formed upon heating suitable alduronic acids in which formation of a 1-4 or gamma-lactone structure is possible, or in which formation of a 1-5 or delta-lactone structure is possible. The alduronic acids are a group of compounds which are obtainable by oxidation of the terminal alcohol group of aldoses. The penturonic acids can be converted to penturonolactones using similar methods.

The sugar acid lactone can be present in the compositions provided herein in an amount from about 0.5 wt % to about 60 wt %. For example, the sugar acid lactone can be present in an amount of from about 1 wt % to about 10 wt %, or from about 2 wt % to about 20 wt %, or from about 5 wt % to about 25 wt %, or from about 10 wt % to about 40 wt %, or from or from about 15 wt % to about 35 wt %, or from about 5 wt % to about 50 wt %, or from about 12 wt % to about 60 wt %. It is to be understood that all values and ranges between these values and ranges are encompassed by the compositions and methods provided herein.

4. Carboxylic Acid

In some embodiments, the antimicrobial compositions provided herein include a carboxylic acid. In embodiments where the slow hydrolyzing acid is present in an amount greater than 40 wt % of the antimicrobial composition, carboxylic acid often is not present because the slow hydrolyzing acid alone can modulate the pH of the solution resulting from dissolution of the antimicrobial composition to a pH of about 7 or lower within about 24 hours at room temperature. A carboxylic acid can be included if desired. For example, a carboxylic acid can be included to accelerate the decrease in the pH of the solution.

It has been discovered that including a carboxylic acid in combination with the hydrogen peroxide generator, the peracid acid catalyst and the slow hydrolyzing acid results in a synergistic interaction, e.g., allowing a reduction in the amount of hydrogen peroxide generator or peracid acid catalyst or both required to generate equivalent amounts of PAAH, or interacting with the slow hydrolyzing acid to modulate the decrease in pH. In the antimicrobial compositions provided herein where the amount of slow hydrolyzing acid is greater than 20 wt % based on the weight of the antimicrobial composition, but is less than the amount of hydrogen peroxide generator present, a carboxylic acid generally is included.

Any carboxylic acid known in the art compatible with the other components of the composition can be used. The carboxylic acid can be a straight chain aliphatic carboxylic acid or a branched chain aliphatic carboxylic acid or a combination thereof. Exemplary carboxylic acids include acetic acid, ascorbic acid, citric acid, formic acid, fumaric acid, gluconic acid, glutaric acid, glycolic acid, lactic acid, sorbic acid, succinic acid and sulfamic acid and combinations thereof. In some embodiments, the carboxylic acid is selected from the group consisting of acetic acid, citric acid, formic acid, gluconic acid, glycolic acid, lactic acid, maleic acid, malic acid, oxalic acid, succinic acid and tartaric acid. In some embodiments, the compositions include citric acid, alone or in combination with another carboxylic acid. In some embodiments, the antimicrobial compositions include TAED or TAMD or a combination thereof as the peracetic acid catalyst, sodium percarbonate as the hydrogen peroxide generator, glucono-delta-lactone as the slow hydrolyzing acid, and citric acid as the carboxylic acid.

The carboxylic acid can be present in the compositions provided herein in an amount from about 0.5 wt % to about 25 wt %. For example, the carboxylic acid can be present in an amount of from about 1 wt % to about 10 wt %, or from about 2 wt % to about 20 wt %, or from about 5 wt % to about 25 wt %, or from about 0.5 wt % to about 15 wt %, or from about 5 wt % to about 20 wt %. It is to be understood that all values and ranges between these values and ranges are encompassed by the compositions and methods provided herein.

5. Forms

The compositions provided herein generally are provided in a dry form. The dry form is shelf stable for extended periods of time, and readily can be dissolved in a solvent, such as water, to produce a solution containing a peracid. The compositions provided herein can be provided in any dry form known in the art, e.g., as a powder, flake, agglomerate, granule, tablet, capsule, pellet, puck, brick, briquette, block, unit dosage, layered compression or composite. Any one of the powder, flake, agglomerate, granule, tablet, capsule, pellet, puck, brick, briquette, block, unit dosage, layered compression or composite can be dissolved in a solvent to provide the composition in the form of a liquid.

Any appropriate solvent can be used to dissolve the composition to provide it in liquid form. In some embodiments, the solvent is predominately water. The water can be deionized water, distilled water, hard water, city water, well water, water supplied by a municipal water system, water supplied by a private water system, or treated water. In general, hard water refers to water having a level of calcium and/or magnesium ions in excess of about 100 ppm. For example, hard water containing 400 ppm calcium carbonate can be used to dissolve the solid forms of the compositions provided herein.

The dry form of the composition can be dissolved in a solvent to provide a liquid form of the composition. In some embodiments, the solution is substantially aqueous, meaning that while the majority of the solvent in the liquid form is water, non-water solvents can be present. In some embodiments, the liquid form of the compositions provided herein contain a non-water solvent in an amount that its less than about 25 wt % of the composition. In some embodiments, the liquid form of the compositions provided herein contain a non-water solvent in an amount that its less than about 10 wt % of the composition. In some embodiments, the liquid form of the compositions can contain a non-water solvent in an amount between about 5 wt % and about 25 wt %, or about 1 wt % and about 10 wt %, or about 0.05 wt % and about 5 wt %. It is to be understood that all values and ranges between these values and ranges are encompassed by the compositions and methods provided herein.

6. Effervescent Formulations

In some embodiments, the compositions provided herein are formulated to be an effervescent composition. The effervescent composition is water soluble and rapidly disintegrates. In some embodiments, the effervescent composition dissolves to a clear solution when placed in excess water at room temperature in less than 5 minutes, or even in less than 2 minutes. The uniformity and clarity of the composition can be determined by viewing with the naked eye.

To formulate the compositions provided herein to be effervescent, an effervescent generator can be included. In some embodiments, the effervescent generator includes an acid and a base. When contacted with a solvent that includes water, the effervescent generator is activated, liberating the acid and base, which react with each other to produce a gas, e.g., carbon dioxide gas.

Examples of useful acids included in the effervescent generator include citric acid, ascorbic acid, aspartic acid, malic acid, adipic acid, tartaric acid, fumaric acid, succinic acid, sodium acid pyrophosphate, lactic acid, and mixtures thereof. The acid can be present in the effervescent generator in an amount of from 10 wt % to about 60 wt %, or from about 15 wt % to about 50 wt %, or from about 25 wt % to about 40 wt %, based on the weight of the effervescent generator.

The base of the effervescent generator is capable of generating a gas, such as carbon dioxide. Examples of suitable carbonate bases include sodium bicarbonate, sodium carbonate, sodium sesquicarbonate, potassium carbonate, potassium bicarbonate, calcium carbonate, magnesium carbonate, magnesium oxide, sodium glycine carbonate, and mixtures thereof. The effervescent generator can include a base in an amount of from about 10 wt % to about 60 wt %, or from about 15 wt % to about 50 wt %, or from about 25 wt % to about 40 wt %, based on the weight of the effervescent generator. In some embodiments, the effervescent generator includes an alkali metal carbonate and an acid. The alkali metal carbonate can be anhydrous potassium carbonate, hydrated potassium carbonate, anhydrous sodium carbonate, or hydrated sodium carbonate or a combination thereof. The amount of effervescent generator included in the antimicrobial compositions provided herein can vary, such as in an amount from about 1 wt % to about 30 wt % by weight of the antimicrobial composition. It is to be understood that all values and ranges between these values and ranges are encompassed by the compositions and methods provided herein.

7. Protective Layer

The compositions provided herein can include a protective layer. The protective layer protects the composition from the influence of physical or chemical action applied from the surroundings. The protective layer can be on or around or encapsulating any of the solid forms of the antimicrobial compositions provided herein. In some embodiments, the protective layer can be in the form of a film, packet, pouch, sheath or envelope that surrounds the solid form of the antimicrobial composition. The protective layer can contain or be made of a material that dissolves or disperses rapidly when exposed to water, thereby releasing the contained solid form of the antimicrobial composition to the water.

For example, the protective layer can be made of or contain any film forming water soluble polymer, such as water soluble polyvinyl alcohol, polyvinylpyrrolidone, cellulose derivatives such as sodium cellulose acetate propionate sulfate and hydroxypropyl methyl cellulose (HPMC), xanthan gum, alginate, gellan gum, gelatin, modified starch or any combination thereof. Methods of preparing water soluble or dispersible pouches are described, e.g., in U.S. Pat. Nos. 2,760,942; 3,086,007; 3,198,740; 3,374,195; 3,413,229; 3,892,905; 4,155,971; 4,340,491; 4,416,791; 4,608,187; and 4,626,372; and in WO 02/042400 and WO 2008/087424. The thickness of the protective layer can be any appropriate thickness. For example the protective layer can have a thickness of from about 10 µm to about 2500 µm thick. The protective layer can be prepared so that when applied to the compositions provided herein, the final dried protective layer adds from at or about 0.01 wt % to at or about 10 wt % based on the weight of the composition. The protective layer can be in the form of a water soluble or dispersible protective pouch. The thickness of the film used to produce the pouch can be up to 5 mm, but can be 2 mm or less, or 1 mm or less, and can be 25 µm to 250 µm thick.

The protective pouch can be provided as a multi-compartment pouch, containing two or more compartments. For example, the pouch can be a two-compartment pouch, where the first compartment includes a hydrogen peroxide generator in combination with a peracid catalyst, and the second compartment includes a slow hydrolyzing acid. In some embodiments, the pouch can include three or more compartments. For example, the pouch can be a three-compartment pouch, where the first compartment includes a hydrogen peroxide generator, a second compartment includes a peracid catalyst, and the third compartment includes a slow hydrolyzing acid. The multi-component pouch can be or contain the same film forming polymers described above. In some embodiments, the pouch is made of or contains water soluble polyvinyl alcohol. Methods of preparing water soluble or dispersible multi-component pouches are described, e.g., in U.S. Pat. Nos. 5,224,601; 6,655,837; 6,995,126; 7,013,623; and 7,036, 986.

The protective pouch can be used to provide unit dosages of the antimicrobial compositions, pre-weighed for addition to a predetermined amount of solvent, such as water. For example, the protective pouch can contain an amount of an antimicrobial composition provided herein to make a spray bottle solution of a hard surface sanitizing or disinfectant spray when dissolved in water, or an amount that makes a sanitizer or disinfectant for mop buckets when added to a standard industrial bucket, or a laundry sanitizer or disinfectant when added to the water in a washing machine, or surgical instrument sanitizer when added to water in an instrument sterilizing tray.

A polymer coating also can be applied to the surface of the solid form of the antimicrobial composition, e.g., agglomerate, granule, flake, tablets, capsules, pellet, puck, brick, briquette, block, layered compression or composite as a protective layer. Any polymer coating known in the art can be used. Suitable coating materials can include adipic acid, azelaic acid, glutaric acid, malonic acid, oxalic acid, pimelic acid, sebacic acid, suberic acid, succinic acid, undecanedioic acid, dodecanedioic acid, tridecanedioic acid, hydroxypropyl cellulose, hydroxypropyl methylcellulose (e.g., Opadry® coating), polyvinylacetate, hydroxyethyl cellulose, methylhydroxyethyl cellulose, methyl cellulose, ethyl cellulose (e.g., Surelease® coating), cellulose acetate, sodium carboxymethyl cellulose, polymers and copolymers of acrylic acid and methacrylic acid and esters thereof (e.g., Eudragit® RL, Eudragit® RS, Eudragit® L100, Eudragit® S100, Eudragit® NE), starch, modified starch, matlodextrin, a wax, gum arabic, shellac, water soluble polyvinyl alcohol, polyalkylene glycols, acrylic polymer, such as sodium polyacrylate, or polyvinylpyrrolidone, or combinations thereof. In some embodiments, the polymer coating is or contains a water soluble polyvinyl alcohol or a polyalkylene glycol. Exemplary polyalkylene glycols include polyethylene glycol and polypropylene glycol. When used, the molecular weight of the polyalkylene glycol is selected to be in the range of about 400 to about 8000.

When present, the polymer coating can be applied to any desired thickness or weight gain. In some embodiments, the weight gain due to the application of a protective polymer is from about 0.1 wt % to about 10 wt %, or from about 0.5 wt % to about 5 wt %, or from 1 wt % to about 8 wt %. It is to be understood that all values and ranges between these values and ranges are encompassed by the compositions and methods provided herein.

A polymer coating as a protective layer can be applied to a solid form of an antimicrobial composition provided herein. Exemplary solid forms to which a protective layer can be applied are agglomerates, granules, and tablets. In some embodiments, a polymer coating can be applied to agglomerates or granules, the coated agglomerates or granules then can be compressed into a tablet, and a protective layer applied to the tablet. The composition of each protective layer independently is selected.

The polymer coating as a protective layer can be applied to the solid form of an antimicrobial composition provided herein using any appropriate method known in the art. For example, a polymer coating can be applied by conventional coating techniques such as, e.g., pan coating, fluidized bed coating, fluidized bed bottom sprayed coating, air suspension coating, compression coating, spray drying, spray congealing, solvent evaporation, melting, coacervation, or interfacial complexation or any combination thereof. The polymer solution or suspension used to form the polymer coating can be in a conventional coating pan, or, alternatively, using an automated system such as a Fluidized Bed Processor (e.g., those available from Glatt Air Techniques Inc., Ramsey, N.J.) or a top spray or bottom spray fluid bed coaters (e.g., Precision Coater™, available from Niro Inc., Columbia, Md.).

The protective layer of the antimicrobial compositions provided herein, whether in the form of a water soluble or dispersible pouch or as a polymer coating on the surface of the solid form of the composition, provides a means for minimizing human contact with the components of the antimicrobial composition. This makes the antimicrobial compositions provided herein safer to handle by consumers, keeping the consumer from directly contacting the hydrogen peroxide generator, peracid catalyst and slow hydrolyzing acid of the composition, reducing possible interaction with exposed skin and eyes.

The scientific rationale of the US EPA's Design for the Environment (DfE) program is of the highest importance for setting the standards for what should be recognized as truly environmentally friendly ("green") chemistry as well as being safe for human interaction. Under these DfE guidelines, one must present chemistry that is not only fit for passing the established EPA testing required to obtain a disinfectant registration but that also is safer for consumers to use.

DfE requires that a registered disinfectant chemistry is not only acceptable to their environmental, pollution, aquatic toxicity and biodegradation limits but also does not carry a signal word stronger than CAUTION. There is a need in the marketplace for green and safer disinfection chemistries. Thus, provided herein is a disinfectant composition that utilizes the PAAH technology stemming from sodium percarbonate and catalyzed by TAED and that also will pass the safety testing for skin and eye irritation so as not to have to carry a signal word at all, or only to the extent of the signal word CAUTION. The disinfectant compositions provided herein accomplishes the disinfection while remaining safer to handle by humans. One way in which this is accomplished is by using a polymer technology that coats the dangerous chemistries in dry form and reduces the possible interaction with exposed skin and eyes.

The antimicrobial compositions provided herein can be disinfectant compositions that include, or are partially or completely covered, enveloped or contained within, a protective polymer. In some embodiments, the protective polymer comprises an acrylic, a sugar, a starch, a wax, a resin, a polyvinyl alcohol or a combinations thereof. In some embodiments, the protective polymer comprises polyvinyl alcohol and is the form of a water soluble pouch. The pouch separately can carry the solid forms of the hydrogen peroxide generator and peracetic acid catalyst. In some embodiments, the protective polymer comprises a glycol. In some embodiments, the protective polymer is or comprises a polyethylene glycol. In some embodiments, the protective polymer is or comprises a maltodextrin.

The antimicrobial compositions provided herein can be provided in a dry form, e.g., a polyvinyl alcohol (PVA) packet, powder or compressed tablet, that when dissolved in an aqueous solvent makes (a) a spray bottle solution of a hard surface sanitizing or disinfectant spray; or (b) a sanitizer or disinfectant for mop buckets; or (c) a laundry sanitizer or disinfectant; or (d) a laundry machine sanitizer or disinfectant; or (e) a solution that sanitizes or disinfects industrial or household appliances, such as a coffee maker, stove, oven, microwave, range, sink, refrigerator, freezer, toaster, washing machine, dryer or bottle washer; or (f) a solution that disinfects surgical instruments, alone or in combination with ultrasonication.

The solutions prepared by dissolving the antimicrobial compositions provided herein in a solvent can include additional components. For example, the solutions can include a chelating agent, sodium bisulfate, a polyglycol, a polyalkylene glycol, a methoxypolyalkylene glycol, a polyglycol copolymer, a hexitol, a siloxane, a polysilane, a polysiloxane, a silicone detergent, sodium carbonate, sodium gluconate, polyethylene glycol, an acrylic acid homopolymer, a surfactant, a bleaching agent, a bleach activator, an optical brightener, an anti-redeposition agent, a color, or a fragrance or any combination thereof. Exemplary bleaching agents include bleach activators, hydrogen peroxide, sources of hydrogen peroxide, pre-formed peracids, alkali metal hypochlorites, monochloramine, dichloramine, alkali metal dichloroisocyanurates, chlorinated trisodium phosphate and mixtures thereof.

D. Methods of Preparation

1. Preparation of the Compositions

The antimicrobial compositions provided herein can be prepared by blending together the hydrogen peroxide generator, peracid catalyst and slow hydrolyzing acid (and when present the carboxylic acid) to form a mixture in which the powders are evenly distributed and homogeneous. Any powder blending technique that results in a uniform final product can be used. Known devices, such as a Hobart® planetary mixer, a vee-blender, a vee-cone blender, a rotary batch mixer, a fluidized bed mixer, a ribbon blender, a paddle blender and a plow blender or combinations thereof, can be used to mix the components. The mixing can be carried out at room temperature under atmospheric pressure, and is not adversely affected by temperature or pressure conditions. High humidity has a negative impact on the blending. A dehumidification system can be used in the blending area to maintain a relative humidity of about 25% or less, or 15% or less. Any dehumidification system known in the art can be used to control humidity (e.g., any of the dehumidification systems available from Munters AB, Kista, Sweden). The amount of time required to form a uniform blend can depend on the amount of material to be blended and the size and type of mixing equipment selected. The antimicrobial compositions provided herein are not adversely affected by the time of mixing. In some embodiments, a vee-cone blender large enough so that no more than 50% of its capacity is used to contain the components is used to mix the components for 1 hour to obtain a uniform mixture.

2. Preparation of Agglomerates or Granules

In some embodiments, the uniform blend of the components of the antimicrobial composition can be agglomerated to form larger-sized agglomerates or granules. In some embodiments, the agglomerates or granules are free-flowing. The uniform blend can be agglomerated using any granulation process, such as wet granulation, dry granulation, fluid bed granulation, or a combination thereof, either alone or in the presence of an excipient such as a binder. Any binder that is effective in forming the agglomerate and creating a stable agglomerated structure can be selected. Exemplary binders include polyvinyl alcohol, polyethylene glycol, an alcohol, anionic and nonionic surfactants, film forming polymers, fatty acids, fatty acid polyol esters, polyglycols, hexitols, and fatty alcohol oxyalkylates and combinations thereof.

Agglomerates can be prepared using any conventional agglomeration equipment that facilitates mixing and intimate contacting of a liquid binder with the components of the antimicrobial composition such that it results in agglomerated particles. The agglomerated particles can take the form of flakes, prills, noodles, ribbons, agglomerates or granules. In some embodiments, a preferred form is a granule. Suitable agglomerators for use in the production of agglomerates include vertical agglomerators (e.g. Schugi Flexomix or Bepex Tirboflex), rotating drums, and pan agglomerators.

In some embodiments, the solid form of the antimicrobial compositions provided herein, such as a uniform blend of the components of the antimicrobial composition or agglomerates or granules thereof, can be formed into a tablet, or filled into a capsule, or be provided in a dissolvable pouch, in order to provide a unit dosage form of the antimicrobial compositions provided here.

3. Tablet Preparation

In some embodiments, the solid form of the antimicrobial compositions provided herein, such as a uniform blend of the components of the antimicrobial composition or agglomerates or granules thereof, can be formed into a tablet. Tablets have several advantages over powdered products: they do not require measuring and are thus easier to handle and dispense for preparation of a disinfectant solution, and they are more compact, facilitating more economical storage and reducing shipping costs.

A tablet containing any of the antimicrobial compositions provided herein can be of any geometric shape. Exemplary shapes include spherical, cube, disk, rod, triangular, square, rectangular, pentagonal, hexagonal, lozenge, modified ball, core rod type (with hole in center), capsule, oval, bullet, arrowhead, compound cup, arc triangle, arc square (pillow), diamond, half-moon and almond. The tablets can be convex or concave. The tablets can be flat-faced plain, flat-faced bevel-edged, flat-faced radius edged, concave bevel-edged or any combination thereof. In some embodiments, the tablet can have a generally axially-symmetric form and can have a round, square or rectangular cross-section. The tablet can be of uniform composition, or can contain two or more distinct regions having differing compositions. For example, in some embodiments, the tablets contain one distinct region containing a hydrogen peroxide generator, another distinct region containing a peracid catalyst and another distinct region containing a slow hydrolyzing acid. In some embodiments, the tablets contain one distinct region containing a combination of a hydrogen peroxide generator and a peracid catalyst, and another distinct region containing a slow hydrolyzing acid and a carboxylic acid.

Tablets containing the tablet binding composition provided herein can be prepared using any method known in the art, including compression, casting, briquetting, injection molding and extrusion. In some embodiments, the tablet preferably is produced by compression, for example in a tablet press. Direct compression often is considered to be the simplest and the most economical process for producing tablets. Direct compression requires only two principal steps: the mixing of all the ingredients and compressing this mixture into a tablet. Any method known in the art for formation of a tablet can be used to prepare a tablet containing the antimicrobial compositions provided herein. For example, the components of the antimicrobial composition can be prepared by admixing the components to achieve a uniform mix. Any powder blending, mixing or shaking technique that results in a uniform final product can be used. Known devices, such as a Hobart® planetary mixer, a vee-blender, a vee-cone blender, a rotary batch mixer, a fluidized bed mixer, a ribbon blender, a paddle blender and a plow blender or combinations thereof, can be used to mix the components. The uniform blend can be blended with lubricants or other excipients prior to tableting.

The resulting uniform mix then can be placed into a die of the desired geometry in a conventional tablet press, such as a single stroke or rotary press. The press includes a punch suitably shaped for forming the tablet. The uniform mix is then subjected to a compression force sufficient to produce a tablet, and a tablet containing the antimicrobial composition provided herein is ejected from the tablet press. Agglomerates and granules also can be used to form tablets. The agglomerates or granules can be blended with lubricants or other excipients prior to tableting.

Any tableting equipment known in the art can be used for tablet formation. Suitable equipment includes a standard single stroke or a rotary press. Such presses are commercially available, and are available from, e.g., Carver, Inc. (Wabash, Ind.), Compression Components & Service, LLC (Warrington, Pa.), Specialty Measurements Inc. (Lebanon, N.J.), GEA Pharma Systems (Wommelgem, Belgium), Korsch America Inc. (South Easton, Mass.) or Bosch Packaging Technology (Minneapolis, Minn.).

The tablets containing any of the antimicrobial compositions provided herein can have any desired diameter, such as a diameter of between about 5 mm and about 75 mm. In some embodiments, the tablets have a diameter of at least 6 mm, at least 7 mm, at least 8 mm, at least 9 mm, at least 10 mm, at least 15 mm, at least 20 mm, at least 25 mm, at least 30 mm, at least 35 mm, at least 40 mm, at least 45 mm, at least 50 mm, at least 55 mm, at least 60 mm or at least 70 mm. The tablets containing an antimicrobial composition provided herein can be of any weight, such as a weight between 100 mg and 100 g. In some embodiments, the tablet can have a total weight of about 1 g to about 30 g, or from about 5 g to about 25 g, or from about 10 g to about 30 g. It is to be understood that all values and ranges between these values and ranges are encompassed by the compositions and methods provided herein.

The tableting can be carried out at room temperature under atmospheric pressure, and is not adversely affected by temperature or pressure conditions. High humidity has a negative impact on tableting. A dehumidification system is used in the tableting area to maintain a relative humidity of about 25% or less, or 15% or less. Any dehumidification system known in the art can be used to control humidity (e.g., any of the dehumidification systems available from Munters AB, Kista, Sweden).

The tablet can be compressed by applying a compression pressure of at least about 1500 PSI, preferably at least 1750 PSI. In some embodiments, the tablet can be compressed applying a compression pressure of at least 2000 PSI, or at least 2500 PSI, or at least 5000 PSI, or at least 7500 PSI, or at least 10,000 PSI. In some embodiments, the tablet can be compressed applying a compression pressure from about 1750 PSI to about 20,000 PSI. In some embodiments, the tablet can be compressed applying a compression pressure in the range of about 1750 PSI to about 15,000 PSI, or from about 1800 PSI to about 15,000 PSI, or from about 1850 PSI to about 12,500 PSI, or from about 1900 PSI to about 10,000 PSI, or from about 2000 PSI to about 9500 PSI, or from about 1750 PSI to about 8500 PSI, or from about 1750 PSI to about 7500 PSI, or from about 1750 PSI to about 5500 PSI. The compression pressure can be selected to most economically provide optimum tablet integrity and strength (measured, e.g., by tablet hardness), and having the desired product aesthetics and dissolution characteristics.

E. Packaged Systems

The solid form or the liquid form of the antimicrobial composition can include a packaging material to form a packaged system. The packaging material can be rigid or flexible, and can be composed of any material suitable for containing the appropriate form of the antimicrobial compositions provided herein. Examples of suitable packaging materials include glass, metal foil, treated metal foil, metal foil pouches, plastic, plastic film, plastic sheets, blister packs, cardboard, cardboard composites, paper and treated paper, and any combination thereof.

The packaged system can include a container for dissolving the formulation in a solvent to form an antimicrobial composition solution, or a receptacle for containing and/or dispensing the formulation and solvent, or both a container and a receptacle. In some embodiments, the receptacle can be used for preparing, dispensing and storing the antimicrobial composition solution. Any receptacle capable of containing the antimicrobial composition solution can be included in the packaged system. In particular, the receptacle can include a spray bottle, a sponge, a conventional hand sprayer container, an electric spray dispenser container (see U.S. Pat. Nos. 5,716,007 and 5,716,008), a bucket, a can, a drum, a towelette, a wipe, or a pad or any combination thereof.

F. Articles Of Manufacture

The antimicrobial compositions provided herein can be part of an article of manufacture, which can include a container suitable for containing the compositions, such as for shipping and/or storage. The antimicrobial compositions provided herein can be stored or shipped in a variety of containers, and the containers can be made of or contain any of a variety of container materials, such as glass, acrylonitrile butadiene styrene (ABS), high impact polystyrene, polycarbonate, high density polyethylene, low density polyethylene, high density polypropylene, low density polypropylene, polyethylene terephthalate, polyethylene terephthalate glycol and polyvinylchloride and combinations thereof. The containers can include barrier films to increase storage stability. Suitable barrier films can include nylons, polyethylene terephthalate, fluorinated polyethylenes, and copolymers of acrylonitrile and methylmethacrylate.

An article of manufacture can include an antimicrobial composition provided herein and a set of instructions, such as for the use of the antimicrobial compositions. In some applications, the article of manufacture includes instructions for preparing a cleaning/disinfectant solution by dissolving one of the antimicrobial compositions provided herein in an appropriate solvent. The article of manufacture can include one of the antimicrobial compositions provided herein and storage instructions, or a material safety data sheet or a combination thereof. The article of manufacture can include one of the antimicrobial compositions provided herein and a dispenser or applicator for preparing or for use with the cleaning or disinfectant solution prepared by dissolution of the antimicrobial composition, alone or in combination of any of storage instructions, preparation instructions or a material safety data sheet.

G. Applications

The antimicrobial compositions provided herein can be provided as powder, flake, agglomerate, granule, tablet, capsule, pellet, puck, brick, briquette, block, unit dosage, layered compression or composite. Any one of these can include a protective polymer. The protective polymer can be in the form of a dissolvable pouch or packet.

In some embodiments, the antimicrobial compositions are provided in unit dosage forms, such as compressed tablets, capsules, pellets, pucks, bricks, briquettes, blocks or as dissolvable pouches or packets that can be added to a predetermined amount of solvent to prepare a liquid form of the antimicrobial composition. For example, when dissolved in a solvent, such as water, the antimicrobial compositions provided herein produce sanitizing or disinfectant solutions. For example, a PVA packet, powder or compressed tablet containing an antimicrobial composition provided herein can be used to make a spray bottle solution of a hard surface sanitizing or disinfectant spray, or a sanitizer or disinfectant for mop buckets, or a laundry sanitizer or disinfectant, or a laundry machine sanitizer or disinfectant, or a solution that sanitizes or disinfects industrial or household appliances, or a solution that disinfects surgical instruments. The amount of antimicrobial composition in the solution can be from about 0.05 wt % to about 5 wt % of the solution (about 0.5 g/L to about 50 g/L). In some embodiments, the amount of antimicrobial composition in the solution can be from about 0.1 wt % to about 1 wt % of the solution (about 1 g to about 10 g/L).

The sanitizing or disinfectant solutions can be applied in any situation where it is desired to sanitize or disinfect a surface. The sanitizing or disinfectant solutions are particularly well suited for treating hard surfaces. Such hard surfaces can be found in private households as well as in commercial, medical, institutional and industrial environments. The hard surfaces can be made of or contain any number of different materials, e.g., enamel, ceramic, glass, stainless steel, chrome, vinyl, linoleum, melamine, glass, fiberglass, Formica®, granite, marble, hardwood, grout, porcelain, concrete, plastic, plastified wood, metal or any painted or varnished or sealed surface. In some embodiments, the sanitizing or disinfectant solutions containing the an antimicrobial composition provided herein sanitizes or disinfects the hard surface within 5 minutes of application.

A sanitizing or disinfecting solution containing an antimicrobial composition provided herein can be used on any surface. Exemplary hard surfaces include, but are not limited to, bathroom surfaces (e.g., floor, drains, tub, shower, mirrors, sinks, toilet, toilet seat, urinal, bidet, lavatory pans, countertops, shower doors or curtains, shower stalls, wash basins, bathroom fixtures, windows, fans, walls, light fixtures and tiles); appliance surfaces (e.g., coffee maker, stove, oven, range, sink, garbage disposal, dishwashers, refrigerator, freezer, microwave, toaster, mixers, washing machine, dryer, barbeque); kitchen surfaces (e.g., appliances, floor, fixtures, light fixtures, fans, countertops, crockery, cupboards, cutlery, doors, door handles, walls, tables, chairs, cabinets, drawers, food processing equipment, flatware, utensils, floors, glassware, phones, clocks, plate ware, shelves, pantry, sinks, dishwashers, windows, and work surfaces); transportation devices (e.g., cars, bicycles, snowmobiles, motorcycles, off-road-vehicles, tractors, recreation vehicles, boats, and planes); yard equipment; farm equipment; laboratory surfaces (e.g., autoclaves, work surfaces, hoods, clean rooms, storage rooms, cold rooms, countertops, centrifuges, and floors); computer surfaces (keyboards, monitors, housing, towers, laptops, and cables); hand rails; banisters; dental equipment or devices; medical devices or equipment; patient care equipment; patient monitoring equipment; surgical devices or equipment or instruments; veterinarian equipment; tools; and utility devices (e.g., telephones, radios, televisions, entertainment centers, stereo equipment, CD and DVD players, play stations, and analog and digital sound devices). Countertops can include tile surfaces, granite, marble or other stone surfaces, Corian® or other manmade hard surfaces, engineered quartz such as Viatera® quartz surfaces (LG Hausys), wood surfaces, glass surfaces, acrylic or polyester resin surfaces, concrete surfaces and stainless steel surfaces.

In some embodiments, the hydrogen peroxide generator is sodium percarbonate, calcium peroxide, urea peroxide, sodium persulfate, potassium monopersulfate (Oxone®, DuPont™, Wilmington, Del.) or a combination thereof. In some embodiments, the peracid catalyst is a peracetic acid catalyst. In some embodiments, the peracetic acid catalyst is tetraacetyl ethylenediamine. In some embodiments, the slow hydrolyzing acid is a glucono-delta-lactone, delta-gluconolactone, D-glucofuranurono-6,3-lactone, glucurolactone or a combination thereof. In some embodiments, the carboxylic acid is citric acid. In some embodiments, the antimicrobial composition provided herein includes sodium percarbonate, tetraacetyl ethylenediamine, glucono-delta-lactone and optionally citric acid.

In some embodiments, the formulations containing an antimicrobial composition provided herein can include a metal protectant. In some embodiments, the metal protectant is a corrosion inhibitor. Exemplary corrosion inhibitors include $C_4$-$C_{16}$ alkyl pyrrolidones, $C_1$-$C_{18}$ alkylamines, benzoates, azoles, imidazoles, diazoles, triazoles, aromatic triazoles and their salts, such as benzotriazole, tolyltriazole, sodium tolyltriazole, monosodium phosphate, disodium phosphate, sodium hexametaphosphate, and potassium equivalents thereof, hydroxyethylidine di-phosphonic acid, 8-hydroxyquinoline, orthophenylphenol, sarcosine, and sarcosinate corrosion inhibitors.

Preferred metal protectants include sarcosine and sarcosinate corrosion inhibitors. Sarcosinate corrosion inhibitors include sarcosine and salts thereof, and sarcosinate surfactants, and any combination thereof. Exemplary sarcosinate corrosion inhibitors include cocoyl sarcosine, lauroyl sarcosine, myristoyl sarcosine, N-acyl sarcosine, oleoyl sarcosine, and stearoyl sarcosine and the sodium salts, potassium salts or amine salts thereof, and sarcosinate surfactants or any combination thereof. In some embodiments, the corrosion inhibitor can include sodium cocoyl sarcosinate, sodium lauroyl sarcosinate, sodium myristoyl sarcosinate, sodium N-acyl sarcosinate, sodium oleoyl sarcosine, or sodium stearoyl sarcosine or any combination thereof.

An exemplary composition that can be used to make a hard surface sanitizer spray composition containing an antimicrobial composition provided herein by dissolving the composition in an aqueous solvent, such as water, is a compressed tablet containing about 20 wt %-30 wt % sodium percarbonate, about 10 wt %-20 wt % TAED, about 10 wt %-35 wt % citric acid, about 20 wt %-40 wt % sodium bicarbonate, about 1 wt %-5 wt % polyethylene glycol, about 5 wt %-25 wt % glucono-delta-lactone, and optionally a surfactant, such as a linear alcohol ethoxylate (e.g., Tomadol® 25-7, Air Products and Chemicals, Inc., Allentown, Pa., USA), which when present can be in an amount of about 0.05 wt % to about 5 wt %. The sanitizer spray composition can include a bleach activator. The compressed tablet can be of any size, such as from about 1 gram to about 25 grams, and one or more than one tablet can be used to make an aqueous solution of the antimicrobial composition for use as a surface sanitizing spray. A sufficient number of tablets can be added to a quantity of solvent, such as water, to yield a solution containing from about 0.1 wt % to about 1 wt % of the hard surface sanitizer composition (1-10 g/L).

Another exemplary composition that can be used to make a hard surface sanitizer spray composition containing an antimicrobial composition provided herein by dissolving the composition in an aqueous solvent can be provided as a powder, flake, tablet, agglomerate or granule, containing about 45 wt %-55 wt % sodium percarbonate, about 10 wt %-20 wt % TAED, about 10 wt %-20 wt % glucono-delta-lactone, about 5 wt %-20 wt % citric acid, and optionally a polyalkylene glycol, such as a polyethylene glycol or a polypropylene glycol, which when present can be in an amount of up to about 10 wt %. In some embodiments, the hard surface sanitizer composition is in the form of a compressed tablet having a weight from about 2 g to about 30 g, and a sufficient number of tablets is added to a quantity of solvent, such as water, to yield a solution containing from about 0.1 wt % to about 5 wt % of the hard surface sanitizer composition (1-50 g/L).

An exemplary automatic dishwasher sanitizer containing an antimicrobial composition provided herein can be a powder, flake, tablet, agglomerate or granule containing about 40 wt %-60 wt % sodium percarbonate, about 20 wt %-35 wt % TAED, about 10 wt %-35 wt % citric acid, about 20 wt %-40 wt % sodium bicarbonate, about 1 wt %-5 wt % polyethylene glycol, about 0.5 wt %-20% glucono-delta-lactone, and optionally a chelating agent, which when present can be in an amount of up to about 5 wt %. Exemplary chelating agents include methylglycine diacetic acid, trisodium salt (MGDA, Trilon® M, BASF Corporation, Florham Park, N.J., USA), citric acid, diethylene triamine pentaacetic acid (DTPA), ethylene diamine tetraacetic acid (EDTA), ethylene glycol tetraacetic acid (EGTA), glutamic acid diacetic acid (GLDA), glutamic acid, and mixtures thereof (see U.S. Pat. No. 5,688,516). A preferred chelating agent is MGDA.

An exemplary automatic laundry machine sanitizer containing an antimicrobial composition provided herein can be a powder, flake, tablet, agglomerate or granule containing about 40 wt %-60 wt % sodium percarbonate, about 20 wt %-35 wt % TAED, about 0.5 wt %-20 wt % glucono-delta-lactone, about 10 wt %-35 wt % citric acid, and optionally a polyalkylene glycol, such as a polyethylene glycol or a polypropylene glycol, which when present can be in an amount of up to about 5 wt %. The laundry machine sanitizer composition can include a polyglycol, a polyalkylene glycol, a methoxypolyalkylene glycol, a polyglycol copolymer, a surfactant, a siloxane, a polysilane, a polysiloxane or any combination of these ingredients.

An exemplary dental, medical or surgical instrument soaking solution containing an antimicrobial composition provided herein can be preparing by dissolving in a solvent a powder, flake, tablet, agglomerate or granule of an antimicrobial composition provided herein containing about 40 wt %-60 wt % sodium percarbonate, about 20 wt %-35 wt % TAED, about 5 wt %-30 wt % glucono-delta-lactone and optionally up to about 20 wt % citric acid. The antimicrobial composition can be present in the solvent in an amount from about 0.1 wt % to about 5 wt % of the soaking solution (1-50 g/L). The surgical instrument soaking formulation can include a metal protectant. The metal protectant can include a corrosion inhibitor. For example, the formulation can include from about 0.1 wt % to about 5 wt % of a sarcosinate corrosion inhibitor. The surgical instrument soaking formulation can be used in conjunction with an ultrasonic bath to clean and sanitize the instruments. In some embodiments, the surgical instrument soaking formulation can include an enzyme, alone or in combination with an additional component. The enzyme can be a lipase, a protease, a peroxidase, an oxidase, an amylolytic enzyme, a cellulase, a polyesterase, a glucanase, an amylase, a glucoamylase, a glycosidase, a hemicellulase, a mannanase, a xylanase, a xyloglucanase, a pectinase, a 3-glucosidase, or any combination thereof. The surgical instrument soaking formulation can include one or more surfactants. Exemplary surfactants include cationic, anionic, nonionic and amphoteric surfactants.

An exemplary closed system sanitizer formulation containing an antimicrobial composition provided herein can be a powder, flake, tablet, agglomerate or granule containing about 45 wt %-55 wt % sodium percarbonate, about 20 wt %-30 wt % TAED, about 5 wt %-20 wt % glucono-delta-lactone and about 5 wt %-20 wt % citric acid. In some embodiments, the closed system sanitizer formulation is in the form of a compressed tablet having a weight from about 20 g to about 30 g, and one tablet can be used for sanitizing a dishwasher or laundry machine. In some embodiments, the closed system sanitizer formulation is in the form of water soluble pouch containing from about 20 g to about 30 g of granules of the antimicrobial composition, and one pouch can be used for sanitizing a dishwasher or laundry machine. The closed system sanitizer formulation can include a metal protectant. The metal protectant can include a corrosion inhibitor. For example, the formulation can include from about 0.1 wt % to about 5 wt % of a sarcosinate corrosion inhibitor.

In some embodiments, the formulations containing an antimicrobial composition provided herein can include a bleach activator. Exemplary bleach activators include an acylated alkylene diamine, benzoyl peroxide, benzoyl caprolactam, tetraacetyl glycouril, N-acylated hydantoine, hydrazine, triazole, hydratriazine, urazole, di-ketopiperazine, sulfurylamide, 6-nonyl-amino-6-oxoperoxy-caproic acid, cyanurate, a carboxylic acid anhydride, decanoyloxybenzenesulphonate sodium-acetoxy-benzene sulfonate, sodium-benzoyloxy benzene sulfonate, sodium-lauroyloxybenzene sulfonate, sodium-isononanoyloxy benzene sulfonate, acylated sugar derivatives, pentaglucose, nonanoyloxybenzene sulfonate, and combinations thereof. The bleach activator can be present in an amount that is at least about 0.5 wt % by weight of the formulation.

Application Methods

The solutions prepared by dissolving the antimicrobial compositions provided herein in a solvent can be applied to surfaces by any technique or method known in the art. Exemplary application methods include spraying, wiping, direct application, immersion, or as part of a normal cleaning process, such as part of a laundry washing or dishwashing process. The solution can be applied directly to a surface as a spray or fine mist, via a woven or nonwoven substrate, brush, sponge, wipe or cleaning pad, or any combination thereof.

Also provided are methods of disinfecting or sanitizing a surface. The methods include contacting the surface with a liquid containing an antimicrobial composition provided herein. The method also can include preparing a liquid containing an antimicrobial composition provided herein by dissolving the antimicrobial composition in a solvent. The solvent can include water, an alcohol, an aldehyde, or a ketone or a combination thereof. In some embodiments, the solvent is or contains water.

The methods provided herein can result in the destruction of, or prevention of the growth of, a microbe on a hard surface. The microbe can be any one or a combination of a bacteria, archaea, unicellular and filamentous algae, unicellular and filamentous fungi (such as yeasts and molds), unicellular and multicellular parasites, and viruses.

The methods provided herein can result in killing bacteria on the treated surface, for example to prevent the spread of the bacteria. The methods also can inhibit the growth of bacteria on a treated surface. Exemplary bacteria that could be treated with a cleaning or disinfecting solution containing an antimicrobial composition provided herein include *Acinetobacter, Burkholderia, Campylobacter, Clostridium, Enterococcus, Escherichia, Helicobacter, Klebsiella, Legionella, Listeria, Meningococcus, Mycobacterium, Pseudomonas, Salmonella, Shigella, Staphylococcus* and *Streptococcus*.

Exemplary sanitizer formulations of the antimicrobial compositions provided herein were tested for their ability to kill bacteria on a solid non-food-contact surface using the EPA Non-Food Contact Surface Sanitizer Test (DIS/TSS-10, 1976). The tested sanitizer formulations contained PAAH in an amount of from about 125 ppm to about 200 ppm. The tested bacteria included *S. aureus* and *K pneumoniae*. The test measured the sanitizing ability on a non-food contact surface with a 5 minute exposure at ambient temperature. The number of surviving colony forming units of bacteria after treatment was compared to treatment with a sterile distilled water control to determine the percent reduction of bacteria by the test sanitizer. The tested sanitizer formulations containing the antimicrobial compositions provided herein killed >99.999% of *S. aureus* and *K. pneumoniae* within 5.0 minutes of exposure at ambient temperature.

In some embodiments, a color indicator can be included in the dry form of the composition. In some embodiments, the color indicator is a temporary non-persistent color indicator. In some embodiments, the color indicator is a pH indicator that has a color change in the range of from about 7 to about 9. When a pH indicator having a first and second color state is used, the first color state of the pH indicator yields a solution of a first color that can indicate that the solution is not yet ready for use as a surface sanitizer, while the second color state of the pH indicator, evidencing that the pH was become more acidic, results in a color change in the solution, indicating that the solution is ready for use as a surface sanitizer. Examples of pH indicators that can be included in the formulations provided herein include thymolphthalein, phenolphthalein, cresol red, phenol red, 4-nitrophenol, thymol blue and bromothymol blue and any combination thereof. For example, when phenolphthalein is used, the initial color of the resulting solution of the composition is bright fuchsia, which with time changes to faint pink to colorless, indicating that the solution is ready for use as a cleaning or disinfecting solution. When phenol red is used, the initial color of the resulting solution of the composition is bright fuchsia, which with time changes to red to orange, indicating that the solution is ready for use as a cleaning or disinfecting solution. When bromthymol blue is used, the initial color of the resulting solution of the composition is blue, which with time changes to green, indicating that the solution is ready for use as a cleaning or disinfecting solution.

When present, the amount of the color indicator, such as a pH indicator, included in an antimicrobial composition provided herein generally is from about 0.005 wt % to about 1.0 wt % based on the weight of the composition. In some embodiments, the amount of the color indicator in the antimicrobial composition can be from about 0.05 wt % to about 0.5 wt %. The amount included in the composition can be dictated by the color indicator selected. Generally, the amount of color indicator is selected so that the amount in the final solution is not too high resulting in a color change time that is too long or that may cause staining, and not so low that the resulting solution has an insufficiently intense color.

Tablet Weight Loss

Tablets that lose more than 0.5% of their original weight are indicative of tablets with poor tablet qualities like rough edges, die wall streaking and tablet face sticking. The amount of tablet weight loss during the manufacturing process can be measured using any technique known in the art. As an exemplary method, the initial amount of material added to the die is recorded, and after the tablet is made via compression, the tablet is weighed. The difference between the weight of the tablet and the initial amount of material added to the tablet die is the "weight loss" value. Tablets that exhibit a weight loss of more than 0.5% are deemed to exhibit poor tablet qualities.

H. Examples

The following examples are included for illustrative purposes only and are not intended to limit the scope of the embodiments provided herein.

Examples 1 and 2

Exemplary Antimicrobial Compositions without Carboxylic Acid

Antimicrobial compositions containing a hydrogen peroxide generator, a peracetic acid catalyst, and a slow hydrolyzing acid, where the ratio of the hydrogen peroxide generator to the peracetic acid catalyst is between 1.5:1 and 3:1 respectively, were prepared. Sodium percarbonate was used as the hydrogen peroxide generator, tetraacetylethylenediamine (TAED) was used as the peracetic acid catalyst, and glucono-delta-lactone (GDL) was used as the slow hydrolyzing acid. The components of the compositions are shown in Table 1.

TABLE 1

| | Antimicrobial Composition. | | | | |
| --- | --- | --- | --- | --- | --- |
| Example | Sodium Percarbonate[1] (%) | TAED[2] (%) | GDL[3] (%) | Solution Initial pH | Solution pH @ 24 hr. |
| 1 | 33.3 | 11.1 | 55.6 | 8.37 | 4.84 |
| 2 | 33.86 | 22.57 | 43.75 | 8.26 | 6.92 |

[1] = available from Solvay Chemicals, Bruxelles, Belgium
[2] = available from Warwick Chemicals, Flintshire, UK
[3] = available from Jungbunzlauer Suisse AG, Basel, Switzerland To prepare the antimicrobial compositions, each of the indicated amounts of the components was placed in a laboratory scale vee-cone blender (Munson Machinery Company, Inc., Utica, N.Y.). The components were blended for 5 minutes to achieve a homogeneous blend.

Aqueous solutions of the antimicrobial compositions of Examples 1 and 2 were prepared as follows. 9 g of the composition was dissolved in 91 g water to yield a solution containing about 3% sodium percarbonate, 1% TAED and 5% GDL.

The pH of the solution was measured upon dissolution of the composition in tap water, and measured again after the solution was maintained at room temperature for 24 hours at ambient pressure and humidity. The results are shown in Table 1. The data shows that, when a antimicrobial composition containing greater than 40 wt % GDL was dissolved in a solvent to form a solution, the solution containing the antimicrobial composition had an initial alkaline pH, which favors peracid (PAAH) formation, followed by an automatic decrease in the pH over time to an acidic pH (e.g., less than pH 7), stabilizing the peracid (PAAH) in the solution. No carboxylic acid was needed to reduce the pH to a pH in the acidic range within 24 hours at room temperature.

Examples 3 Through 6

Exemplary Antimicrobial Compositions with Carboxylic Acid

Formulations containing citric acid were prepared to investigate an observed synergy when a carboxylic acid is used in conjunction with the slow hydrolyzing acid. Antimicrobial compositions containing a hydrogen peroxide generator, a peracetic acid catalyst, a slow hydrolyzing acid, and a carboxylic acid, where the ratio of the hydrogen peroxide generator to the peracetic acid catalyst is between 1.5:1 and 3:1 respectively, were prepared. Sodium percarbonate was used as the hydrogen peroxide generator, tetraacetylethylenediamine (TAED) was used as the peracetic acid catalyst, glucono-delta-lactone (GDL) was used as the slow hydrolyzing acid and citric acid was used as the carboxylic acid. The components of the compositions are shown in Table 2.

TABLE 2

Antimicrobial Composition containing a carboxylic acid.

| Ex. | Sodium Percarbonate[1] (%) | TAED[2] (%) | GDL[3] (%) | Citric Acid[4] (%) | Solution Initial pH | Solution pH @ 24 hr. |
|---|---|---|---|---|---|---|
| 3 | 26 | 15 | 54 | 5 | 8.48 | 5.24 |
| 4 | 31.65 | 10.55 | 52.6 | 5.2 | 8.0 | 4.45 |
| 5 | 33.86 | 22.57 | 28.57 | 15 | 9.01 | 6.52 |
| 6 | 42.32 | 14.11 | 28.57 | 15 | 9.37 | 6.87 |

[1]= available from Solvay Chemicals, Bruxelles, Belgium
[2]= available from Warwick Chemicals, Flintshire, UK
[3]= available from Jungbunzlauer Suisse AG, Basel, Switzerland
[4]= available from S.A. Citrique Beige N.V., Tienen, Belgium To prepare the antimicrobial compositions, each of the indicated amounts of the components was placed in a laboratory scale vee-cone blender (Munson Machinery Company, Inc., Utica, N.Y.). The components were blended for 5 minutes to achieve a homogeneous blend. An aqueous solution of each of the antimicrobial compositions of Examples 3 and 4 was prepared as follows. For Example 3, 6.65 g of the composition was dissolved in 93.35 g tap water to yield a solution containing about 1.73% sodium percarbonate, 1% TAED, 3.6% GDL and 0.33% citric acid. For Example 4, 9.5 g of the composition was dissolved in 90.5 g water to yield a solution containing about 3% sodium percarbonate, 1% TAED, 5% GDL and 0.5% citric acid. For Example 5 and 6, 10 grams of each formulation separately was dissolved in 90 gram water to produce 1% solutions of the formulations.

The pH of each solution was measured upon dissolution of the composition in tap water, and measured again after the solution was maintained at room temperature for 24 hours at ambient pressure and humidity. The results are shown in Table 2 above. The data shows that the solution containing the antimicrobial composition for each of Examples 3, 4, 5 and 6 has an initial alkaline pH, which favors peracid (PAAH) formation, followed by an automatic decrease in the pH after 24 hours to an acidic pH (e.g., less than pH 7), stabilizing the peracid (PAAH) in the solution.

Example 7

Tablets

A homogeneous blend of each of the compositions of Example 1 to 6 separately was used to prepare tablets. A 20 gram aliquot of each one of the homogeneous blend of Examples 1 to 6 was weighed to be made into a compressed tablet. Each 20 gram powder sample was compressed into a tablet using a 38.1 mm diameter die. Tablet compression was performed using a CARVER Press (Carver, Inc. (Wabash, Ind.)) with a 7500 PSI gauge. For the compositions of Example 1 to 6, tablets were made at a pressure of 5500 PSI. All of the tablets exhibited smooth face surfaces, had good edges and good side walls with few defects, and had low weight loss (less than 0.5%).

Example 8

Measurement of ppm PAAH

Aqueous sanitizer compositions were aseptically prepared to measure the amount of PAAH produced. Two replicates of three different preparations of the antimicrobial composition described in Example 1 were prepared. One gram of each of the three lots separately was placed in sterilized volumetric flasks and a quantity of synthetic hard water (400 ppm $CaCO_3$), prepared according to AOAC Official Methods, 960.09 (E), was added to prepare a 1 liter solution and the flask was mixed until product was dissolved.

The aqueous solutions were assayed to measure the peracetic acid concentration using a permanganate titration analysis. Titrations were performed quickly with constant stirring of the sample. An initial titration to measure background contamination was performed. Using a 250 mL Erlenmeyer flask, 70 mL deionized water was mixed with 20 mL of 25% sulfuric acid solution under constant stirring. One drop of 0.1 N $KMnO_4$ was added to the acid (blank) solution. A pale pink color that persisted for at least 60 seconds indicated there were no contaminants and that the blank equaled zero. To the same solution, 0.4 g of KI crystals and 1 mL of 1% starch solution was added, resulting in a blue color. 0.01 N $Na_2S_2O_3$ immediately was titrated into the solution until a colorless endpoint that persisted for at least 60 seconds was achieved and the amount of $Na_2S_2O_3$ used was recorded. The blank titration was performed in duplicate, the amount of $Na_2S_2O_3$ used was averaged and subtracted as background in the calculation to determine % PAAH, as discussed below.

The sample was diluted by weighing an appropriate volume of the test solution into a clean beaker and transferring quantitatively to a 1000 ml volumetric flask. The sample beaker was washed with deionized water and the rinsing solutions also were transferred into the volumetric flask. The volumetric flask was filled to volume with deionized water and the contents mixed thoroughly.

The test sample was analyzed by adding 20 mL deionized water to a 250 mL Erlenmeyer flask and with constant mixing, adding 20 mL of a 25% sulfuric acid solution. 50 ml of the diluted test sample solution was pipetted into the 250 ml flask with mixing, and titrated with 0.1 N $KMnO_4$ until a first faint pink color that persisted for at least 60 seconds appeared. To this solution, 0.4 g of KI crystals were added, resulting in the development of a yellow color. Immediately, the solution was titrated with 0.01 N $Na_2S_2O_3$ until pale yellow in color. 1.0 mL of a 1% starch solution was added and a blue color developed. With constant mixing, titration continued until a colorless water-clear endpoint that persisted for at least 60 seconds was achieved. The total mL of $Na_2S_2O_3$ used in the titration was recorded. Each sample was tested in duplicate and the two titrant volumes averaged.

The % PAAH was calculated using the formula:

$$\% \, PAAH = \frac{([mL \, Na_2S_2O_3 \, sample] - [mL \, Na_2S_2O_3 \, blank]) \times 0.01 \, N \times 38.025 \times 100}{(g \, sample/1000) \times 50 \times 1000}$$

where:
in the numerator, 38.025=equivalent weight of peracetic acid; and
100=percent conversion; and
in the denominator, "g sample/1000"=dilution of sample;
50=the number of mL of test solution used; and
1000=mL to L conversion.

To convert the value to ppm PAAH, the % PAAH value was multiplied by 10,000. The results are shown in Table 3.

TABLE 3

Peracetic acid (PAAH) Concentration of solutions.

| Example | Replicate | Sample Wt. (g) | ppm PAAH | Avg. ppm PAAH |
|---|---|---|---|---|
| 8-A | 1 | 100.00 | 120 | 125 |
|  | 2 | 100.00 | 130 |  |
| 8-B | 1 | 100.00 | 170 | 170 |
|  | 2 | 100.00 | 170 |  |
| 8-C | 1 | 100.00 | 200 | 205 |
|  | 2 | 100.00 | 210 |  |

The data show that the solutions of this formulation produced PAAH in the range of from about 125 ppm to about 200 ppm.

Examples 9 Through 14

Comparative Solutions with Different Ratios of Sodium Percarbonate to TAED

In order to demonstrate that a ratio of between 1.5:1 and 3:1 for the hydrogen peroxide generator to the peracetic acid catalyst is necessary to achieve the automatic decrease in pH to an acidic pH with time in the antimicrobial compositions provided herein, solutions containing a ratio of hydrogen peroxide generator and peracetic acid catalyst outside of the recited range of ratios were prepared. The components of each of the solutions is shown in Table 4.

TABLE 4

Comparative solutions outside of the recited ratio of peroxide generator to peracid catalyst.

| | Component (wt %) | | | | Ratio (peroxide generator to TAED) | Solution pH | |
|---|---|---|---|---|---|---|---|
| Example | Sodium Percarbonate[1] | TAED[2] | GDL[3] | Citric Acid[4] | | Initial pH | pH @ 24 hr. |
| 9 | 5 | 1 | 5 | 0 | 5:1 | 9.25 | 9.00 |
| 10 | 4 | 1 | 5 | 0 | 4:1 | 8.85 | 8.34 |
| 11 | 5 | 5 | 5 | 0 | 1:1 | 8.71 | 7.93 |
| 12 | 5 | 1 | 5 | 5 | 5:1 | 8.8 | 8.79 |
| 13 | 5 | 1 | 10 | 1 | 5:1 | 8.43 | 8.14 |
| 14 | 5 | 5 | 5 | 1 | 1:1 | 8.50 | 7.26 |

[1] = available from Solvay Chemicals, Bruxelles, Belgium
[2] = available from Warwick Chemicals, Flintshire, UK
[3] = available from Jungbunzlauer Suisse AG, Basel, Switzerland
[4] = available from S.A. Citrique Beige N.V., Tienen, Belgium Each solution was prepared by dissolving the components in the tap water with mixing until dissolved. The pH was measured upon dissolution of the components in the water, and measured again after each of the solutions was maintained at room temperature for 24 hours at ambient pressure and humidity.

The data show that solutions containing a ratio of hydrogen peroxide generator to the peracetic acid catalyst below 1.5:1 (e.g., comparative Examples 11 and 14) or solutions containing a ratio of hydrogen peroxide generator to the peracetic acid catalyst above 3:1 (e.g., comparative Examples 9, 10, 12 and 13) do not achieve an automatic decrease in the pH within 24 hours to an acidic pH (e.g., pH less than 7) even when the amount of GDL is doubled (Example 13) or citric acid is added (Examples 12 to 14).

Examples 15 Through 26

Comparative Compositions with Lower Amount of Slow Hydrolyzing Acid

In order to demonstrate that a minimum of 10 wt % slow hydrolyzing acid is necessary in the antimicrobial compositions in order to achieve the desired modulation in pH, comparative solutions containing a ratio of between 1.5:1 and 3:1 for the hydrogen peroxide generator to the peracetic acid catalyst but less than 10 wt % glucono-delta-lactone were prepared. The formulations and results are provided in Table 5. Each comparative formulation was made into a solution by dissolving 1 gram of the formulation into 99 mL water with constant stirring. The pH of each solution was tested 5 minutes after dissolution, and then at 3 hours and 24 hours after dissolution.

TABLE 5 pH of comparative solutions with low amounts of glucono-delta-lactone.

| Ex. # | Component (wt %) | | | | Ratio (peroxide generator to TAED) | pH | | |
|---|---|---|---|---|---|---|---|---|
| | Sodium Percarbonate[1] | TAED[2] | GDL[3] | Citric Acid[4] | | Initial pH | pH @ 3 hr. | pH @ 24 hr. |
| 15 | 55.05 | 36.70 | 8.25 | 0 | 1.5:1 | 10.16 | 8.82 | 8.82 |
| 16 | 68.81 | 22.94 | 8.25 | 0 | 3:1 | 10.24 | 9.9 | 9.72 |
| 17 | 46.05 | 30.70 | 8.25 | 15 | 1.5:1 | 8.18 | 7.47 | 7.16 |
| 18 | 57.56 | 19.19 | 8.25 | 15 | 3:1 | 8.34 | 7.54 | 7.48 |
| 19 | 42.86 | 28.57 | 0 | 28.57 | 1.5:1 | 6.87 | 6.85 | 8.67 |
| 20 | 33.86 | 22.57 | 0 | 43.57 | 1.5:1 | 4.61 | 4.43 | 5.48 |
| 21 | 55.05 | 36.70 | 0 | 8.25 | 1.5:1 | 9.2 | 9.21 | 8.38 |
| 22 | 46.05 | 30.70 | 0 | 23.25 | 1.5:1 | 8.67 | 8.54 | 9.17 |
| 23 | 53.37 | 17.86 | 0 | 28.57 | 3:1 | 6.09 | 6.17 | 8.24 |
| 24 | 42.32 | 14.11 | 0 | 43.57 | 3:1 | 4.2 | 4.08 | 4.83 |
| 25 | 68.81 | 22.94 | 0 | 8.25 | 3:1 | 9.54 | 9.41 | 9.04 |
| 26 | 57.56 | 19.19 | 0 | 23.25 | 3:1 | 5.94 | 5.91 | 6.98 |

[1] = available from Solvay Chemicals, Bruxelles, Belgium
[2] = available from Warwick Chemicals, Flintshire, UK
[3] = available from Jungbunzlauer Suisse AG, Basel, Switzerland
[4] = available from S.A. Citrique Beige N.V., Tienen, Belgium The data show that in comparative solutions containing some GDL but less than 10 wt %, the pH of the solution decreased over time when compared to the initial pH of the solution, but even after 24 hours the solution pH was not close to neutral unless citric acid was included in the formulation in combination with GDL. Even when the low level of GDL was combined with citric acid, the 24 hour pH of the solution was not in the acidic range. Totally replacing GDL with citric acid alone did not demonstrate the desired modulation in solution pH over time. In some of the solutions containing citric acid without GDL, the initial pH of the solution never became alkaline. Thus, the solution was below the $pK_a$ of the TAED and little if any PAAH was formed. In some of the solutions containing citric acid without GDL, the initial pH of the solution was alkaline and remained alkaline after 24 hours. Thus, any PAAH that was formed was unstable and likely destroyed in the alkaline environment.

Examples 27 Through 31

Comparative Formulations without Carboxylic Acid

It has been determined that formulations in which the amount of slow hydrolyzing acid is greater than 20 wt % of the antimicrobial composition but less than the amount of hydrogen peroxide generator often require a carboxylic acid to modulate the pH over time to a pH in the acidic range. Comparative formulations outside of these parameters were prepared. The formulations and results are provided in Table 6. Each comparative formulation was made into a solution by dissolving 1 gram of the formulation into 99 mL water with constant stirring. The pH of each solution was tested 5 minutes after dissolution, and then at 3 hours and 24 hours after dissolution.

TABLE 6 pH of Comparative Solutions without carboxylic acid.

| Ex. # | Component (wt %) | | | | Ratio (peroxide generator to TAED) | pH | | |
|---|---|---|---|---|---|---|---|---|
| | Sodium Percarbonate | TAED | GDL | Citric Acid | | Initial pH | pH @ 3 hr. | pH @ 24 hr. |
| 27 | 42.86 | 28.57 | 28.57 | 0 | 1.5:1 | 9.54 | 8.03 | 7.47 |
| 28 | 53.37 | 17.86 | 28.57 | 0 | 3:1 | 9.77 | 9.33 | 9.25 |
| 29 | 46.05 | 30.70 | 23.25 | 0 | 1.5:1 | 9.13 | 8.87 | 8.12 |
| 30 | 43.57 | 14.11 | 42.32 | 0 | 3:1 | 8.77 | 8.7 | 8.61 |
| 31 | 57.56 | 19.19 | 23.25 | 0 | 3:1 | 9.38 | 8.98 | 8.51 |

The data show that, in comparative solutions containing GDL in an amount greater than 10 wt % but less than the amount of sodium percarbonate without a carboxylic acid present, the pH of the solution decreased over time when compared to the initial pH of the solution, but even after 24 hours the solution pH was not close to neutral.

Example 32

Appliance Sanitizer Spray Tablet

A tablet to be dissolved in a solvent, such as water, to form a sanitizer spray for appliance surfaces was prepared. 33.86 g sodium percarbonate, 22.57 g TAED, 28.57 g glucono-delta-lactone, and 15 g citric acid were blended in a lab scale vee-blender for 5 minutes to achieve a homogeneous blend. 25 gram aliquots of the homogeneous blend were weighed to be made into compressed tablets. Each 25 gram powder sample was compressed into a tablet using a 38.1 mm diameter die using a CARVER Press at a pressure of 5500 PSI. The tablets exhibited smooth face surfaces, had good edges and good side walls with few defects, and had low weight loss (less than 0.5%). A sufficient number of tablets was added to a quantity of solvent, such as water, to yield a solution containing from about 0.1 wt % to about 1 wt % of the composition (1-10 g/L). For Example 32, one 25 g tablet was added to 975 mL water to yield a 0.25 wt % sanitizing spray solution.

Examples 33 Through 35

Hard Surface Sanitizer Spray Tablets

Formulations for preparing a tablet to be dissolved in a solvent, such as water, to form a sanitizer spray for hard surfaces were prepared. The formulations are provided in Table 7.

TABLE 7

Formulations for exemplary hard surface sanitizer spray tablets.

| Example # | 33 | 34 | 35 |
|---|---|---|---|
| Component | Component (wt %) | | |
| Sodium Percarbonate[1] | 50 | 49 | 33.86 |
| TAED[2] | 18 | 12.5 | 22.57 |
| GDL[3] | 18 | 18.5 | 28.57 |
| Citric Acid[4] | 10 | 10 | 15 |
| Sodium Acetate[5] | 4 | 4 | 0 |
| PEG 8000[6] | 0 | 6 | 0 |

[1] = available from Solvay Chemicals, Bruxelles, Belgium
[2] = available from Warwick Chemicals, Flintshire, UK
[3] = available from Jungbunzlauer Suisse AG, Basel, Switzerland
[4] = available from S.A. Citrique Belge N.V., Tienen, Belgium
[5] = available from Niacet Corporation, Niagara Falls, NY, USA
[6] = available from Dow Chemical Company, Midland, MI, USA The components of each of Examples 33, 34, and 35 separately were blended together in a lab scale vee-blender for 5 minutes to achieve a homogeneous blend. 20 gram aliquots of the homogeneous blend of Examples 33 and 34, and 25 gram aliquots of the homogeneous blend of Example 35, were weighed to be made into compressed tablets. Each aliquot of the homogeneous blend separately was compressed into a tablet using a 38.1 mm diameter die using a CARVER Press at a pressure of 5500 PSI. The tablets exhibited smooth face surfaces, had good edges and good side walls with few defects, and had low weight loss (less than 0.5%).

A sufficient number of tablets was added to a quantity of water to yield a solution containing from about 0.1 wt % to about 1 wt % of the composition (1-10 g/L). For Example 33, one 20 g tablet was added to 980 mL water to yield a 0.2 wt % sanitizing spray solution. After 24 hours at room temperature, the pH of the solution was 6.71. For Example 34, two 20 g tablets were added to 960 mL water to yield a 0.4 wt % sanitizing spray solution. After 24 hours at room temperature, the pH of the solution was 6.89. For Example 35, two 25 g tablets were added to 950 mL water to yield a 0.5 wt % sanitizing spray solution.

Examples 36 and 37

Surgical Instrument Soak Tablet

A tablet to be dissolved in a solvent, such as water, to form a surgical instrument sanitizer soaking solution was prepared. The formulations are provided in Table 8.

TABLE 8

Formulations for exemplary surgical instrument sanitizer tablets.

| Example # | 36 | 37 |
|---|---|---|
| Component | Component (wt %) | |
| Sodium Percarbonate[1] | 38.5 | 37.5 |
| TAED[2] | 22.5 | 21.5 |
| GDL[3] | 24 | 23 |
| Citric Acid[4] | 15 | 14 |
| Perlastan ® L30 sodium lauroyl sarcosinate[5] | — | 4 |

[1] = available from Solvay Chemicals, Bruxelles, Belgium
[2] = available from Warwick Chemicals, Flintshire, UK
[3] = available from Jungbunzlauer Suisse AG, Basel, Switzerland
[4] = available from S.A. Citrique Belge N.V., Tienen, Belgium
[5] = available from Schill and Seilacher GmbH, Boeblingen, Germany The components of each composition were blended in a lab scale vee-blender for 5 minutes to achieve a homogeneous blend. 20 gram aliquots of the homogeneous blend were weighed to be made into compressed tablets. Each 20 gram powder sample was compressed into a tablet using a 38.1 mm diameter die using a CARVER Press at a pressure of 5500 PSI. The tablets exhibited smooth face surfaces, had good edges and good side walls with few defects, and had low weight loss (less than 0.5%).

A sufficient number of tablets was added to a quantity of solvent, such as water, to yield a solution containing from about 0.1 wt % to about 1 wt % of the composition (1-10 g/L). For each of Examples 36 and 37, one 20 g tablet was added to 980 mL water to yield a 0.2 wt % solution.

Example 38

Color Shifting Formulation Tablet

A tablet to be dissolved in a solvent, such as water, to form a sanitizer spray for hard surfaces that changes color when ready for use was prepared. 50 g sodium percarbonate, 18 g TAED, 18 g glucono-delta-lactone, 10 g citric acid, 3.75 g sodium citrate, and 0.25 g phenolphthalein were blended in a lab scale vee-blender for 5 minutes to achieve a homogeneous blend. 20 gram aliquots of the homogeneous blend were weighed to be made into compressed tablets. Each 20 gram powder sample was compressed into a tablet using a 38.1 mm diameter die using a CARVER Press at a pressure of 5500 PSI. The tablets exhibited smooth face surfaces, had good edges and good side walls with few defects, and had low weight loss (less than 0.5%).

A sufficient number of tablets was added to a quantity of solvent, such as water, to yield a solution containing from about 0.1 wt % to about 1 wt % of the composition (1-10 g/L). For Example 38, two 20 g tablets were added to 960 mL water to yield a 0.4 wt % solution. Initially, the solution had a pH of 9, and the solution was a bright fuchsia color. Within about 20 minutes, the solution changed to colorless, and was ready to use as a sanitizer spray for hard surfaces.

While various embodiments of the subject matter provided herein have been described, it should be understood that they have been presented by way of example only, and not limitation. Since modifications will be apparent to those of skill in this art, it is intended that this invention be limited only by the scope of the appended claims.

The invention claimed is:
1. An antimicrobial composition, comprising:
a homogeneous blend comprising in dry form:
a hydrogen peroxide generator;
a peracid catalyst;

a sugar acid lactone selected from the group consisting of a gluconolactone, a galactonolactone, a mannonolactone, a gulonolactone, and a combination thereof in an amount from about 10 wt % to about 60 wt %;
an acetate; and
a carboxylic acid,
wherein the homogeneous blend is formed into a compressed tablet; and wherein:
the ratio of the hydrogen peroxide generator to the peracid catalyst is between 1.5:1 and 3:1 respectively; and
the initial pH of an aqueous solution of the composition upon dissolution is alkaline so that the peracid catalyst is exposed to an alkaline pH to promote formation of a peracid in situ, and the pH of the solution automatically reduces to a pH of about 7 or less within 24 hours at room temperature to stabilize the in situ formed peracid.

2. The composition of claim 1, wherein:
the hydrogen peroxide generator comprises an alkali metal perborate, alkali metal percarbonate, alkali metal perphosphate, alkali metal persilicate or alkali metal persulfate or a combination thereof; or
the hydrogen peroxide generator is sodium percarbonate, calcium peroxide, urea peroxide, sodium persulfate, potassium monopersulfate or a combination thereof.

3. The composition of claim 1, wherein:
the peracid catalyst is an agent that contains an acetyl donor group or an acyl donor group or a combination thereof, wherein the agent contains an —O—C(O)CH$_3$ donor group, an —N—C(O)CH$_3$ donor group, an —O—C(O)R$^1$) donor group or an —N—C(O)R$^2$ donor group, wherein R$^1$ and R$^2$ each individually is C$_1$ to C$_{20}$ alkyl; or
the peracid catalyst is selected from the group consisting of monoacetin, diacetin, triacetin, glucose pentaacetate, lactose octaacetate, mannitol hexaacetate, sucrose octaacetate, N,N,N'N'-tetraacetylethylene-diamine (TAED), N,N,N'N'-tetraacetylmethylene-diamine (TAMD), N-acetyl glycine, N-acetyl-methionine, 6-acetamidohexanoic acid, N-acetyl-L-cysteine, 4-acetamido-phenol, N-acetyl-L-glutamine, and N,N',N'',N'''-tetraacetyl glycoluril (TAGU).

4. The composition of claim 1, wherein the sugar acid lactone is glucono-delta-lactone.

5. The composition of claim 1, wherein the hydrogen peroxide generator is present in an amount of from about 40 wt % to about 60 wt %.

6. The composition of claim 1, wherein the peracid catalyst is present in an amount from about 15 wt % to about 30 wt %.

7. The composition of claim 1, wherein the carboxylic acid is present in an amount from about 5 wt % to about 25 wt %.

8. The composition of claim 1 that:
is contained in a water soluble pouch; or
further comprises a protective layer comprising an acrylic, a sugar, a starch, a malto-dextrin, a polyethylene glycol, a film forming water soluble polymer or a combination thereof.

9. The composition of claim 1, wherein:
the carboxylic acid is a straight chain aliphatic carboxylic acid or a branched chain aliphatic carboxylic acid; or
the carboxylic acid is selected from the group consisting of acetic acid, citric acid, formic acid, gluconic acid, glycolic acid, lactic acid, maleic acid, malic acid, oxalic acid, succinic acid and tartaric acid.

10. The composition of claim 1, further comprising an effervescence generator.

11. The composition of claim 1, further comprising a color indicator that changes color when the pH changes from alkaline to more acidic in an amount from about 0.005 wt % to about 1.0 wt % based on the weight of the composition.

12. The composition of claim 1, wherein:
the hydrogen peroxide generator is sodium percarbonate;
the peracid catalyst is N,N,N'N'-tetraacetylethylenediamine (TAED);
the sugar acid lactone is glucono-delta-lactone; and
the carboxylic acid is citric acid.

13. The composition of claim 12, further comprising a surfactant.

14. The composition of claim 1, further comprising one or more of an additional component selected from the group consisting of an organic solvent, a surfactant, a buffering salt, a tablet lubricant, a fragrance, a colorant, a chelant, an enzyme, an acid, a carbonate, a bicarbonate, a phosphate, a wetting agent, a dispersing agent, a hydrotrope, a rheology control agent, a foam suppressant, a metal protectant, and a corrosion inhibitor, present in an amount from 0.05% to 75% based on the weight of the tablet.

15. The composition of claim 1, further comprising:
a surfactant; and
a chelating agent.

16. The composition of claim 1, further comprising a polyglycol, a polyalkylene glycol, a methoxypolyalkylene glycol, a polyglycol copolymer or a combination thereof.

17. A solution, comprising:
from about 50 wt % to about 99.95 wt % of a solvent; and
from about 0.05 wt % to about 50 wt % of the composition of claim 1 dissolved in the solvent.

18. A method of disinfecting a surface, comprising:
dissolving the composition of claim 1 in a solvent to form a disinfecting solution; and
applying the disinfecting solution to the surface resulting in the destruction of a microbe on the surface.

19. The composition of claim 1, wherein the peracid catalyst is present in an amount from about 15 wt % to about 35 wt %.

* * * * *